(12) United States Patent
Mihailescu et al.

(10) Patent No.: US 9,561,019 B2
(45) Date of Patent: Feb. 7, 2017

(54) METHODS AND SYSTEMS FOR TRACKING AND GUIDING SENSORS AND INSTRUMENTS

(71) Applicant: Speir Technologies Inc., Pleasant Hill, CA (US)

(72) Inventors: Lucian Mihailescu, Pleasant Hill, CA (US); Victor Arie Negut, Berkeley, CA (US)

(73) Assignee: ZITEO, INC., Pleasant Hill, CA (US)

( * ) Notice: Subject to any disclaimer, the term of this patent is extended or adjusted under 35 U.S.C. 154(b) by 198 days.

(21) Appl. No.: 13/789,143

(22) Filed: Mar. 7, 2013

(65) Prior Publication Data
US 2013/0237811 A1 Sep. 12, 2013

Related U.S. Application Data

(60) Provisional application No. 61/699,750, filed on Sep. 11, 2012, provisional application No. 61/607,676, filed on Mar. 7, 2012.

(51) Int. Cl.
*A61B 5/05* (2006.01)
*A61B 8/00* (2006.01)
(Continued)

(52) U.S. Cl.
CPC .......... *A61B 8/5238* (2013.01); *A61B 5/0077* (2013.01); *A61B 5/064* (2013.01); *A61B 5/065* (2013.01);
(Continued)

(58) Field of Classification Search
CPC ............ G06K 7/10732; G06K 7/10594; G06K 7/10881; G06K 7/14; G06K 7/10574; G02B 27/48; G02B 26/10; G02B 19/0085; G02B 27/4244; G02B 27/017; H01S 5/02248; H01S 5/4025; A61B 6/482; A61B 18/20; A61B 8/483; A61B 5/1127; A61B 2560/0443; A61B 2019/5276; A61B 2019/5263; A61B 5/0086; A61B 5/0095; A61B 2019/507; A61B 8/145; A61B 8/4254; A61B 19/20; A61B 2019/5227; A61B 2019/5255; A61B 6/5247; A61B 8/00; A61B 8/4245; A61B 8/4483; A61B 8/4494; A61B 8/463; A61B 19/5212; A61B 1/0005; A61B 6/4441; A61B 6/547; A61B 8/0841; A61B 8/5261; A61B 1/00193; A61B 2019/5257
See application file for complete search history.

(56) References Cited

U.S. PATENT DOCUMENTS 5,453,686 A 9/1995 Anderson
5,891,034 A * 4/1999 Bucholz .................... 600/426
(Continued)

FOREIGN PATENT DOCUMENTS

EP 1795142 A1 6/2007
EP 1795142 B1 6/2008
(Continued)

OTHER PUBLICATIONS

Ansar et al., "Linear Pose Estimation from Points of Lines," IEEE Transactions on Pattern Analysis and Machine Intelligence, May 2003, vol. 25(5), pp. 578-589.
(Continued)

*Primary Examiner* — John P Leubecker
*Assistant Examiner* — Arnaldo Torres Diaz
(74) *Attorney, Agent, or Firm* — Kilpatrick Townsend & Stockton LLP

(57) ABSTRACT

A shared-housing ultrasound transducer and machine-vision camera system is disclosed for registering the transducer's x, y, z position in space and pitch, yaw, and roll orientation with respect to an object, such as a patient's body. The position and orientation are correlated with transducer scan data, and scans of the same region of the object are compared in order to reduce ultrasound artifacts and speckles. The system can be extended to interoperative gamma probes or other non-contact sensor probes and medical instruments. Methods are disclosed for computer or remote guiding of a (Continued)

sensor probe or instrument with respect to saved positions and orientations of the sensor probe.

24 Claims, 19 Drawing Sheets

(51) Int. Cl.

| | | |
|---|---|---|
| G06K 9/00 | (2006.01) | |
| G06K 9/36 | (2006.01) | |
| G06T 15/00 | (2011.01) | |
| H04N 5/225 | (2006.01) | |
| A61B 8/08 | (2006.01) | |
| A61B 5/06 | (2006.01) | |
| A61B 5/00 | (2006.01) | |
| G01S 15/89 | (2006.01) | |
| G01S 17/02 | (2006.01) | |
| G01S 17/66 | (2006.01) | |
| G01S 17/89 | (2006.01) | |
| A61M 37/00 | (2006.01) | |
| A61B 8/13 | (2006.01) | |
| G01S 7/52 | (2006.01) | |

(52) U.S. Cl.
CPC ........... *A61B 8/4245* (2013.01); *A61B 8/4254* (2013.01); *A61B 8/4438* (2013.01); *A61B 8/4444* (2013.01); *A61B 8/462* (2013.01); *A61B 8/463* (2013.01); *A61B 8/483* (2013.01); *A61B 8/5261* (2013.01); *A61B 8/5269* (2013.01); *A61B 34/20* (2016.02); *A61B 90/361* (2016.02); *A61M 37/0069* (2013.01); *G01S 7/52077* (2013.01); *G01S 7/52079* (2013.01); *G01S 15/899* (2013.01); *G01S 17/023* (2013.01); *G01S 17/66* (2013.01); *G01S 17/89* (2013.01); *A61B 8/13* (2013.01); *A61B 8/4427* (2013.01); *A61B 8/485* (2013.01); *A61B 8/5253* (2013.01); *A61B 2090/363* (2016.02); *G01S 7/52065* (2013.01); *G01S 15/8936* (2013.01); *G01S 15/8993* (2013.01)

(56) References Cited

U.S. PATENT DOCUMENTS

| | | | |
|---|---|---|---|
| 6,050,943 A * | 4/2000 | Slayton et al. | 600/439 |
| 6,167,296 A | 12/2000 | Shahidi | |
| 6,216,029 B1 * | 4/2001 | Paltieli | 600/427 |
| 6,390,982 B1 * | 5/2002 | Bova et al. | 600/443 |
| 6,540,679 B2 | 4/2003 | Slayton et al. | |
| 6,628,984 B2 | 9/2003 | Weinberg et al. | |
| 6,754,596 B2 | 6/2004 | Ashe | |
| 6,891,518 B2 | 5/2005 | Sauer et al. | |
| 7,035,897 B1 | 4/2006 | Devereaux et al. | |
| 7,142,905 B2 * | 11/2006 | Slayton et al. | 600/427 |
| 7,292,251 B1 | 11/2007 | Gu et al. | |
| 7,500,795 B2 | 3/2009 | Sandhu | |
| 7,549,961 B1 * | 6/2009 | Hwang | 600/440 |
| 7,606,861 B2 | 10/2009 | Killcommons et al. | |
| 7,809,194 B2 | 10/2010 | Zhang et al. | |
| 7,835,785 B2 | 11/2010 | Scully et al. | |
| 7,912,733 B2 | 3/2011 | Clemments et al. | |
| 7,914,453 B2 * | 3/2011 | Slayton et al. | 600/439 |
| RE42,952 E | 11/2011 | Hu et al. | |
| 8,235,909 B2 * | 8/2012 | Barthe et al. | 600/463 |
| 8,565,860 B2 | 10/2013 | Kimchy et al. | |
| 8,831,708 B2 | 9/2014 | Paladini et al. | |
| 9,040,925 B2 | 5/2015 | Giarmana et al. | |
| 9,119,669 B2 | 9/2015 | Keglovich et al. | |
| 9,129,422 B2 | 9/2015 | Mountney et al. | |
| 9,146,198 B2 | 9/2015 | Wendler et al. | |
| 9,286,732 B2 | 3/2016 | Wendler et al. | |
| 9,345,441 B2 | 5/2016 | Wendler et al. | |
| 2001/0056234 A1 | 12/2001 | Weinberg et al. | |
| 2003/0112922 A1 * | 6/2003 | Burdette et al. | 378/65 |
| 2004/0054248 A1 | 3/2004 | Kimchy et al. | |
| 2005/0104881 A1 * | 5/2005 | Yoshida et al. | 345/419 |
| 2005/0256406 A1 * | 11/2005 | Barthe et al. | 600/444 |
| 2005/0271300 A1 * | 12/2005 | Pina | 382/294 |
| 2005/0285844 A1 * | 12/2005 | Morita et al. | 345/156 |
| 2007/0015987 A1 | 1/2007 | Baviera et al. | |
| 2007/0167712 A1 | 7/2007 | Keglovich et al. | |
| 2007/0225553 A1 * | 9/2007 | Shahidi | 600/103 |
| 2007/0236514 A1 | 10/2007 | Agusanto et al. | |
| 2009/0259123 A1 | 10/2009 | Navab et al. | |
| 2009/0306509 A1 | 12/2009 | Pedersen et al. | |
| 2010/0198068 A1 | 8/2010 | Rivaz et al. | |
| 2010/0266171 A1 | 10/2010 | Wendler et al. | |
| 2010/0268067 A1 * | 10/2010 | Razzaque et al. | 600/424 |
| 2010/0298704 A1 | 11/2010 | Pelissier et al. | |
| 2011/0046483 A1 * | 2/2011 | Fuchs et al. | 600/439 |
| 2011/0098083 A1 * | 4/2011 | Lablans | 455/556.1 |
| 2011/0144451 A1 | 6/2011 | Robertson | |
| 2011/0178373 A1 | 7/2011 | Pacey et al. | |
| 2011/0237945 A1 | 9/2011 | Foroughi et al. | |
| 2011/0306051 A1 | 12/2011 | Sheehan et al. | |
| 2012/0069167 A1 * | 3/2012 | Liu et al. | 348/65 |
| 2012/0128223 A1 | 5/2012 | Rivaz et al. | |
| 2012/0226150 A1 | 9/2012 | Baliciki et al. | |
| 2012/0253200 A1 * | 10/2012 | Stolka et al. | 600/459 |
| 2013/0136302 A1 * | 5/2013 | Nam et al. | 382/103 |
| 2013/0168570 A1 | 7/2013 | Wendler et al. | |
| 2013/0172739 A1 | 7/2013 | Paladini et al. | |
| 2013/0229529 A1 * | 9/2013 | Lablans | 348/169 |
| 2013/0338490 A1 | 12/2013 | Wendler et al. | |
| 2014/0175291 A1 | 6/2014 | Giarmana et al. | |
| 2014/0235921 A1 | 8/2014 | Wendler et al. | |
| 2014/0241600 A1 | 8/2014 | Mountney et al. | |
| 2014/0249402 A1 | 9/2014 | Kimchy et al. | |
| 2014/0369560 A1 | 12/2014 | Wendler et al. | |
| 2015/0065875 A1 | 3/2015 | Friebe et al. | |
| 2015/0305700 A1 | 10/2015 | Wendler et al. | |

FOREIGN PATENT DOCUMENTS

| | | |
|---|---|---|
| EP | 2001389 | 12/2008 |
| EP | 1554987 B1 | 3/2009 |
| EP | 2584957 A1 | 5/2013 |
| EP | 2606825 A1 | 6/2013 |
| EP | 2024761 B1 | 5/2014 |
| EP | 2165215 B1 | 5/2014 |
| EP | 2746815 A1 | 6/2014 |
| EP | 2755556 A1 | 7/2014 |
| EP | 2758131 A1 | 7/2014 |
| EP | 2853223 A1 | 4/2015 |
| EP | 2922471 A1 | 9/2015 |
| EP | 1554987 B2 | 12/2015 |
| JP | 2007/282792 A | 11/2007 |
| WO | 2004/019799 A2 | 3/2004 |
| WO | 2006/127142 A2 | 11/2006 |
| WO | 2007/111570 A2 | 10/2007 |
| WO | 2007/131561 A2 | 11/2007 |
| WO | 2011/161197 A1 | 12/2011 |
| WO | 2013/038011 A1 | 3/2013 |
| WO | 2013/041720 A1 | 3/2013 |
| WO | 2014/080013 A1 | 5/2014 |

OTHER PUBLICATIONS

Chiao et al., "Ocular Examination for Trauma; Clinical Ultrasound Aboard the International Space Station," The Journal of Trauma Injury, Infection and Critical Care, 2005, vol. 58(5), pp. 885-889.
de Cunha et al., "The MIDSTEP System for Ultrasound guided Remote Telesurgery," Proceeding of the 20th Annual International Conference of the IEEE Engineering in Medicine and Biology Society, 1998, vol. 20(3), pp. 1266-1269.
Fofi et al., "A comparative survey on invisible structured light," Proc. SPIE5303, Machine Vision Applications in Industrial Inspec-

(56) References Cited

OTHER PUBLICATIONS tion XII, 90, May 2004, doi: 10.1117/12.525369; http://dx.doi.org/10.1117/12.525369.
Gat, "Imagining Spectroscopy Using Tunable Filters: A Review," Proc. SPIE, vol. 4056, Wavelet Applications VII, 50, Apr. 5, 2000, pp. 50-64.
Gee et al., "Sensorless freehand 3D ultrasound in real tissue: Speckle decorrelation without fully developed speckle," Medical Image Analysis, 10 , 2006, 137-149.
Gibon et al., "Stereotactic Localization in Medical Imaging: A Technical and Methodological Review," Journal of Radiosurgery, 1999, vol. 2(3), pp. 167-180.
Goldsmith et al., "An Inertial-Optical Tracking System for Portable, Quantitative, 3D Ultrasound," IEEE International Ultrasonics Symposium Proceedings, 2008, pp. 45-49, doi:10.1109/ULTSYM.2008.0012.
Goldsmith, "An Inertial-Optical Tracking System for Quantitative, Freehand, 3D Ultrasound," (thesis) Worcester Polytechnic Institute, Dec. 2008, 289 pages.
Hansard et al., Time-of-Flight, Principles, Methods and Applications, Springer Briefs in Computer Science, Springer Publications, Nov. 2012.
Kalman, "A New Approach to Linear Filtering and Prediction Problems," Journal of Basic Engineering, 82 (Series D): 35-45.
LaGrone et al., "A review of training opportunities for ultrasonography in low and middle income countries," Tropical Medicine and International Health, Jul. 2012, vol. 17(7), pp. 808-819.
Lepetit et al., "EPnP: Accurate Non-Iterative O(n) Solution to the PnP Problem," http://upcommons.upc.edu/e-prints/bitstream/2117/10327/1/moreno_ijcv2009.pdf.
Lu et al., "Fast and Globally Convergent Pose Estimation From Video Images," Feb. 18, 1998.
Moreno-Noguer et al., "An Accurate O(n) Solution to the PnP Problem," International Journal of Computer Vision, 2009;81:155-66.
Mercier et al., "A Review of Calibration Techniques for Freehand 3-D Ultrasound Systems," Ultrasound in Med. & Biol., 2005, vol. 31(2), pp. 143-165, doi:10.1016/j.ultrasmedbio.2004.11.001.
Mercier et al., "New prototype neuronavigation system based on preoperative imaging and intraoperative freehand ultrasound: system description and validation," Int. J. Cars, 2011, 6:507-522, doi:10.1007/s11548-010-0535-3.
Mikulik et al., "Telemedicine-Guided Carotid and Transcranial Ultrasound: A Pilot Feasibility Study," Stroke, 2006, pp. 229-230, doi: 10.1161/0.1str.0000196988.45318.97, Downloaded from http://stroke.ahajournals.org/ at Lawrence Berkeley Lab on Jun. 30, 2012.
Mordohai et al., "Real-Time Video-Based Reconstruction of Urban Environments".
Nevatia et al., "Computer Aided Medical Diagnosis and Surgery System: Towards Automated Medical Diagnosis for Long Term Space Missions".
Ng et al., "Light Field Photography with a Hand-held Plenoptic Camera," Stanford Tech Report CTSR 2005-02.
Odell et al., "Next Generation, High Accuracy Optical Tracker for Target Acquisition and Cueing".
Prager et al., "Three-dimensional ultrasound imaging," Proc. IMechE, vol. 224 Part H: J. Engineering in Medicine, pp. 193-223.
Rafii-Tari, "Panorama Ultrasound for Navigation and Guidance of Epidural Anesthesia," A Thesis submitted in partial fulliment of the requirements for the degree of Master of Applied Science, The University of British Columbia, Vancouver, Sep. 2011.
Ren et al., "SAD based Sensor-less Freehand 3D Ultrasound Reconstruction with Adaptive Curve Correction".
Sansoni et al., "State-of-the-Art and Application of 3D Imaging Sensors in Industry, Cultural Heritage, Medicine, and Criminal Investigation," Sensors, 2009, vol. 9, pp. 568-601.
Schneider et al., Development and Testing of a New Magnetic-Tracking Device for Image Guidance.
Sheehan et al., "Expert visual guidance of ultrasound for telemedicine," J Telemed Telecare, 2010, 16(2): 77-82.
Sheehan et al., "Tracking Three Dimensional Ultrasound with Immunity from Ferro-Magnetic Interference," LNCS, 2003, 2879, pp. 192-198.
Stolka et al., "Navigation with Local Sensors in Handheld 3D Ultrasound Initial in-vivo Experience," Proc. of SPIE, vol. 7968 79681J-1, downloaded from http://proceedings.spiedigitallibrary.org on Dec. 12, 2012.
Suenaga et al., "A Tele-instruction system for ultrasound probe operation based on shared AR technology,".
Takacs, "A Portable Ultrasound Guidance and Training System Using High Fidelity Virtual Human Models," Proceeding of the International Conference on Medical Information Visualization—MediVis'06.
Takacs et al., "Compact Anatomically Guided Ultrasound for Casualty Care," First International Conference on Advances in Computer-Human Interaction, IEEE, pp. 120-123, doi:10.1109/ACHI.2008.53.
Wang et al., "The Kinect as an interventional tracking system," Proc. of SPIE, vol. 8316 83160U-1, downloaded from http://spiedigitallibrary.org on Dec. 12, 2012.
Xiao-Shan et al., "Complete solution classification for the perspective-three-point problem," Pattern Analysis and Machine Intelligence, IEEE Transactions on 2003:25:930-43.
Yu et al., "A 3D Freehand Ultrasound System for Multi-view Reconstructions from Sparse 2D Scanning Planes," BioMedical Engineering OnLine, 2011, 10:7.
Zhao et al, "Improved 3D Reconstructions Algorithm for Ultrasound B-scan Image with Freehand Tracker," Proc. of SPIE, vol. 7629, 762914-1.
PCT application No. PCT/US2013/029710, International Search Report and Written Opinion, mailed Apr. 24, 2013, 13 pages.
Extended European Search Report, Apr. 28, 2016, EP Application No. 13758013.0, 11 pages.

* cited by examiner

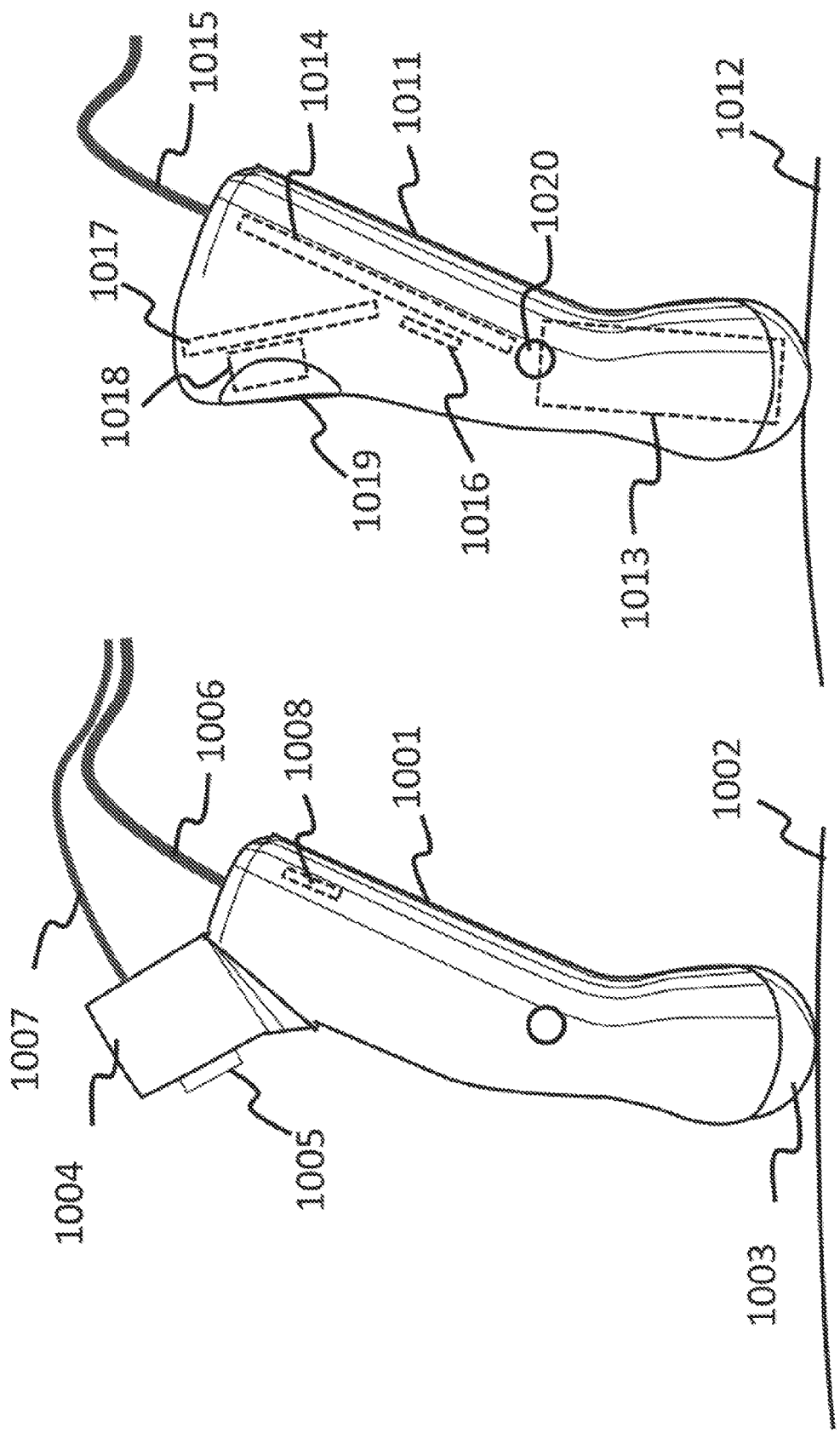

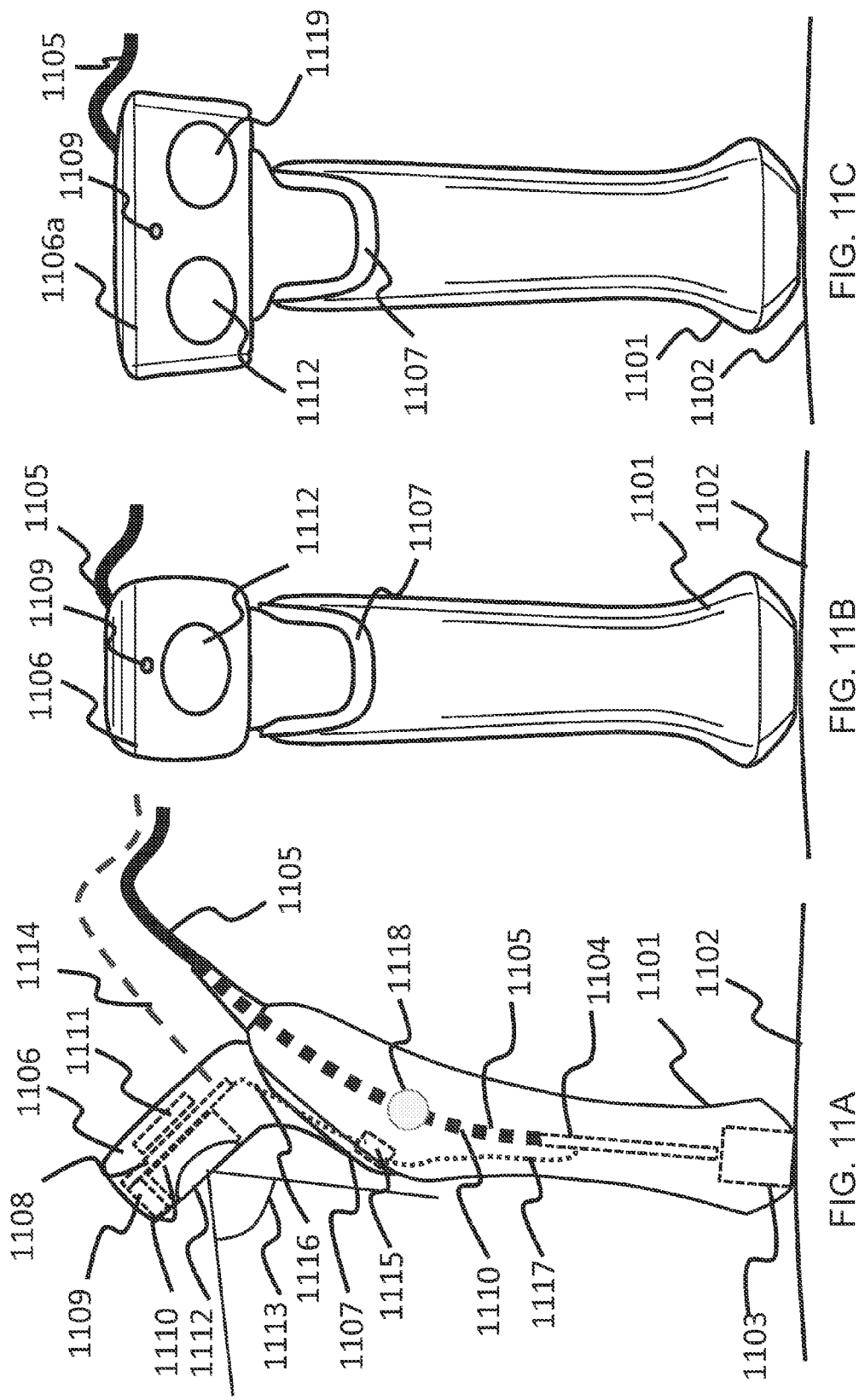

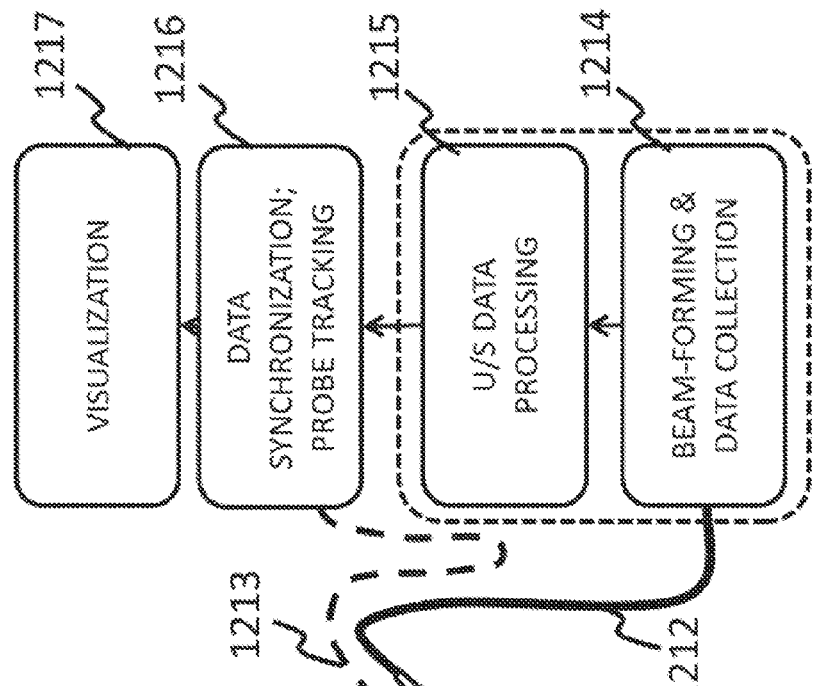
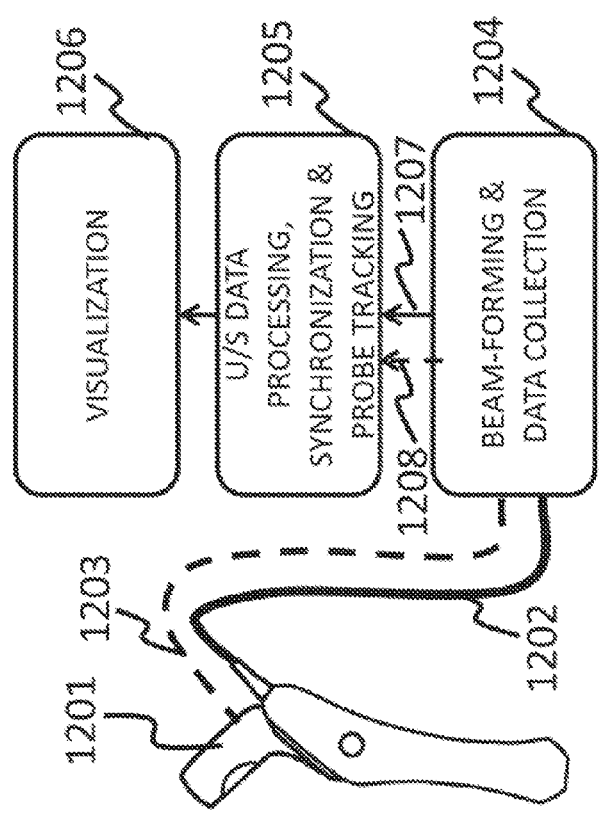

METHODS AND SYSTEMS FOR TRACKING AND GUIDING SENSORS AND INSTRUMENTS

CROSS-REFERENCES TO RELATED APPLICATIONS

This application claims the benefit of U.S. Provisional Application No. 61/699,750, filed Sep. 11, 2012, and U.S. Provisional Application No. 61/607,676, filed Mar. 7, 2012, which are hereby incorporated by reference in their entireties for all purposes.

STATEMENT AS TO RIGHTS TO INVENTIONS MADE UNDER FEDERALLY SPONSORED RESEARCH AND DEVELOPMENT

Not Applicable

BACKGROUND

1. Field of the Invention

Generally, this application relates to position and orientation determination devices for surgery and other contexts. Specifically, this application relates to computer vision and ranging tracking systems for medical instruments and sensor probes.

2. Background

Currently, hand-held sensor systems are being used for several applications, ranging from environmental surveys of chemical, biological and radioactive environments, to medical investigations for diagnostics, disease characterization and intraoperative guiding and imaging. Because they are hand-held, they can be immediately positioned and oriented with almost all of the outstanding flexibility and adaptability of a human operator's hands.

In some instances, a user may wish to know exactly how and where a sensor system is pointed. Yet, the flexibility and adaptability of hand-held sensors also can make them difficult to track. Prior art approaches at spatial registration of sensors and instruments are bulky, cumbersome, expensive, or not practical. There are several examples in which sensor systems were outfitted with a Global Positioning System (GPS) antenna, Inertial Navigation Unit (INU), magnetic sensors, or optical markers.

Unfortunately, GPS only provides coarse, limited spatial resolution and does not work reliably when satellite GPS signals are weak. INU systems drift over time. Magnetic sensors are generally useful for tracking objects within a small volume of space, around 0.1 to 1 square meters ($m^3$). In a controlled laboratory environment, magnetic sensors can provide location resolution of about 1 millimeter (mm) inside volumes around 0.2 $m^3$ and orientation precision to within a degree. However, when used in realistic applications where metallic objects are present, or when other magnetic fields are generated by adjacent electronic equipment, the position resolution decreases to several centimeters within a 0.2 $m^3$ volume. This position resolution is too coarse for many applications, including medical diagnostic and medical interventions where multiple electronic instruments and metallic objects are used. Optical markers attached to probes require a direct and continuous line of sight to an external Coordinate Measuring Machine (CMM) camera system. Generally, CMM camera systems are bulky, expensive and impractical for most applications in where hand-held systems are used or desirable.

U.S. Patent Application No. 2009/0259123 A1 proposes a CMM-type system for tracking hand-held sensors and instruments for intraoperative navigated sentinel lymph node dissection. The system proposed therein uses external infra-red cameras to track coded infrared reflective markers attached to the hand-held probes or hand-held instruments. One drawback of this approach is that a continuous line of sight needs to exist between external cameras placed above a surgery table and all of the markers placed on probes, instruments, and samples. The hands, arms, and heads of the surgeons may easily break the line of sight during surgery procedures.

U.S. Patent Application No. 2012/0253200 A1 uses an augmentation device in the form of a bracketed structure to be appended to an existing imaging probe to project a pattern of structured light onto the skin or an organ of a patient to facilitate stereo object recognition.

There is a need for better, less expensive, and more accurate and precise tracking of hand held sensors and medical instruments.

BRIEF SUMMARY

An ultrasound transducer sharing a housing with a machine-vision camera system is disclosed. The integrated camera views an object, such as a patient's body, and determines the ultrasound transducer's x, y, z position in space and pitch, yaw, and roll orientation with respect to the object. The position and orientation at a point in time are saved along with an ultrasound scan at the same point of time in a record file as a "spatially registered scan." Multiple spatially registered scans of the same region of the body are compared in order to reduce ultrasound artifacts and speckles, and tissue types and elastomeric properties can be refined. A three-dimensional (3-D) model of tissue can be shown to a user.

For an object with many curved surfaces, fiducial markers can be affixed to the object or overlaid as a piece-wise flexible tape. The markers can use two-dimensional coding so that they can be discerned from one another.

The 3-D model can be used for telemedicine and stereotaxy. A remote user of the system or a computer can guide a local human operator or robotic device to move a medical instrument to a particular point on or within a patient's body. Graphical guiding elements such as directional arrows or virtual space renderings can be used to guide a local operator.

Other sensor probes besides ultrasound transducers can be used with spatially registered scans, such as radar, terahertz radiation detectors, intraoperative gamma-ray probes, radiation detectors, radiation dosimeters, and chemical sensors.

Some embodiments of the invention are related to a spatial registration apparatus that includes a rigid housing assembly, an ultrasound transducer having a portion enclosed by the housing, a camera having a portion enclosed by the housing assembly and rigidly connected with the ultrasound transducer, and at least one processor operatively coupled with a memory and the camera, the memory having instructions for execution by the at least one processor configured to determine a spatial position and orientation of the ultrasound transducer with respect to an object using an image captured by the camera.

The memory can have instructions for execution by the at least one processor configured to associate scanning data from the ultrasound transducer with the spatial position and orientation of the ultrasound transducer to create and save a spatially registered scan. The memory can have instructions for execution by the at least one processor configured to reduce an ultrasound artifact or speckle using the saved spatially registered scan and another spatially registered scan. The memory can have instructions for execution by the at least one processor configured to identify a tissue type or elastomeric property using the saved spatially registered scan and another spatially registered scan. The memory can have instructions for execution by the at least one processor configured to construct a three-dimensional (3-D) model of a tissue with respect to the object using the saved spatially registered scan and another spatially registered scan. The memory can have instructions for execution by the at least one processor configured to render a three-dimensional (3-D) structure of the object using the saved spatially registered scan of a first scanning plane and a second spatially registered scan from a second scanning plane. The camera can be selected from the group consisting of an optical camera, an infrared camera, a scanning laser camera, a flash laser camera, a time-of-flight camera, and a structured light camera.

The apparatus can further include a second camera having a portion within the housing, in which the memory includes instructions for execution by the at least one processor configured to determine the spatial position and orientation of the ultrasound transducer with respect to the object using images captured by the cameras. One camera can be a time-of-flight camera while the other camera is a non-time-of-flight camera. An inertial measurement unit (IMU) can be supported by the housing, in which the memory includes instructions for execution by the at least one processor configured to determine the spatial position and orientation of the ultrasound transducer with respect to the object using output from the IMU. A display can be operatively connected with the processor, the display configured for visualizing a three-dimensional (3-D) representation of the object created or refined from the determined spatial position and orientation and output from the ultrasound transducer.

The housing can include multiple housing shells. The memory can have instructions for execution by the at least one processor configured to interpret movements of interactivity elements to execute a process. The camera can be part of a head-mounted tracking and visualization system having a display.

Some embodiments are related to a spatial registration apparatus that includes a medical instrument or sensor probe, a camera rigidly connected with the medical instrument or sensor probe or with a part of a body of a human operator, at least one processor operatively coupled with a memory and the camera, the memory having instructions for execution by the at least one processor configured to determine a current spatial position and orientation of the medical instrument or sensor probe with respect to an object using an image captured by the camera, and at least one processor operatively coupled with a memory, the memory having instructions for execution by the at least one processor configured to derive visualization data from a saved spatially registered scan having a position and orientation corresponding to the current spatial position and orientation of the medical instrument or sensor probe, and display the visualization data to a user.

The user can be remote from or local to the medical instrument or sensor probe.

Some embodiments are related to a spatial registration apparatus that includes a medical instrument or non-imaging sensor probe, a camera rigidly connected with the medical instrument or non-imaging sensor probe or connected with a part of a body of a human operator and at least one processor operatively coupled with a memory and the camera, the memory having instructions for execution by the at least one processor configured to determine a current spatial position and orientation of the medical instrument or non-imaging sensor probe with respect to an object using an image captured by the camera.

The sensor probe can be selected from the group consisting of a radar, a terahertz radiation detector, an intraoperative gamma-ray probe, a radiation detector, a radiation dosimeter, and a chemical sensor. The sensor probe can be an intraoperative gamma-ray probe, wherein the memory has instructions for execution by the at least one processor configured to store radiation count data from the gamma ray probe with the current spatial position and orientation of the gamma-ray probe.

The apparatus can include a fiducial marker, the at least one processor configured to determine the spatial position and orientation of the medical instrument or sensor probe with respect to the object using an image captured by the camera of the fiducial marker on the object. The fiducial marker can include binary coding and/or one or more light emitting diodes (LEDs). The apparatus can include a flexible tape having at least one fiducial marker, the at least one processor configured to determine the spatial position and orientation of the medical instrument or sensor probe with respect to the object using an image captured by the camera of the at least one fiducial marker of the flexible tape on the object. In an embodiment, the object can have a curved surface, such as that of a human body, and the flexible tape is conformed to the curved surface. Each of the at least one fiducial marker can have a rigid substrate, the flexible tape including two or more rigid substrate fiducial markers piece-wise rotatable with respect to each other. The at least one fiducial marker can include multiple fiducial markers, each fiducial marker having a distinct binary coding from one another.

Some embodiments are related to a method for directing a medical procedure. The method includes providing a medical instrument or sensor probe, providing a camera rigidly attached to the medical instrument or sensor probe or connected with a part of a body of a user, calculating a current position and orientation of the medical instrument or sensor probe with respect to an object using an image captured by the camera, and displaying to a user a location of an item of interest or a previously saved position and orientation of a sensor probe with respect to the medical instrument or sensor probe using the calculated current position and orientation.

The displaying can include a graphical guiding element, such as a directional arrow. The displaying can include a three-dimensional (3-D) rendering of the item of interest or previously saved position and orientation of a sensor probe with respect to the object. The method can further include moving the medical instrument or sensor probe in response to the displaying. The user to which the item of interest or previously saved position and orientation is displayed can be remote from or local to the object.

Some embodiments are related to a spatial registration apparatus including a non-optical sensor probe, and a clip interface adapted to detachably and rigidly mate to the sensor probe a portable computing device having a camera and at least one processor operatively coupled with a memory, the memory having instructions for execution by the at least one processor configured to determine a spatial position and orientation of the sensor probe with respect to an object using an image captured by the camera.

The portable computing device can include a smart phone.

Some embodiments are related to a method for spatial registration of sensor probe. The method includes applying a flexible tape having at least one fiducial marker to an object of interest, scanning the object with a sensor probe, imaging, using a camera, the at least one fiducial marker of the flexible tape in order to produce one or more images of the at least one fiducial marker, the scanning and imaging conducted simultaneously, computing a spatial position and orientation of the sensor probe with respect to the object using the one or more images of the at least one fiducial marker, and correlating features of the object detected by the sensor probe using the computed spatial position and orientation.

The method can include conforming the flexible tape to the curved surface. The method can include decoding a binary encoding of a fiducial marker, the correlating using the decoding. The method can include rendering an image of a three-dimensional (3-D) feature of the object using the computed spatial position and orientation. The method can include detachably mating a smart phone to the sensor probe, the smart phone having the camera and performing the imaging, computing, and correlating.

The method can include conforming the flexible tape to a curved surface of the object. The method can also include detachably mating a smart phone to the sensor probe, the smart phone having the camera and performing the imaging, computing, and correlating.

Some embodiments are related to a spatial registration apparatus including an instrument or sensor probe, a fiduciary element attached to the instrument or sensor probe, a camera mechanically connected to a part of the body of a user, the camera aligned to observe an area where the user manipulates the instrument or sensor probe, and at least one processor operatively coupled with a memory and the camera, the memory having instructions for execution by the at least one processor configured to determine a spatial position and orientation of the instrument or sensor probe with respect to an object using an image captured by the camera.

With reference to the remaining portions of the specification, including the drawings and claims, one of ordinary skill in the art will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 10A illustrates an ultrasound probe sharing a housing assembly with tracking and spatial registration camera and IMU in accordance with an embodiment.

FIG. 10B illustrates an ultrasound probe rigid housing assembly with tracking and spatial registration capability enabled by a machine vision system and an IMU mechanically registered to the probe in accordance with an embodiment.

FIG. 11A illustrates a side view of an ultrasound probe assembly with tracking and spatial registration capability enabled by ranging systems and an IMU mechanically registered to the probe in accordance with an embodiment.

FIG. 11B illustrates a rear view of an ultrasound probe assembly with tracking and spatial registration capability enabled by ranging systems and an IMU mechanically registered to the probe in accordance with an embodiment.

FIG. 11C illustrates a rear view of an ultrasound probe assembly with dual-camera tracking and spatial registration capability enabled by ranging systems and an IMU mechanically registered to the probe in accordance with an embodiment.

FIG. 12A illustrates ultrasound readouts with probe tracking capability in accordance with an embodiment.

FIG. 12B illustrates alternative ultrasound readouts with probe tracking capability in accordance with an embodiment.

DETAILED DESCRIPTION

Figure 1:
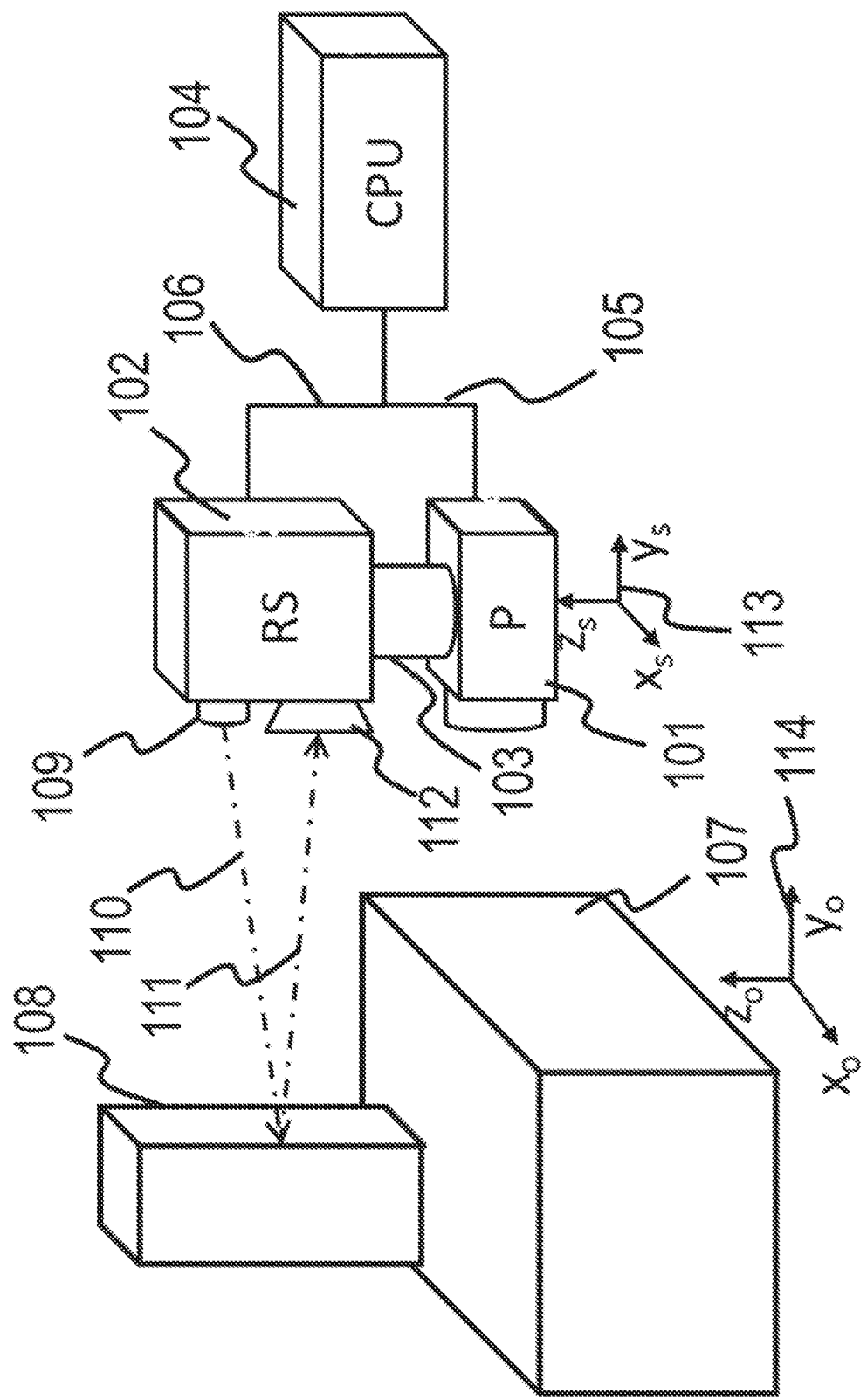
FIG. 1 illustrates tracking and spatial registration of a medical instrument or sensor probe using a ranging device mechanically registered to a probe in accordance with an embodiment.

Herein are described methods and systems using these methods aimed at providing position and orientation (or spatial registration) for various instruments, such as hand-held probes, sensors, scanners, imagers or other instruments, with respect to investigated objects and environmental objects. An instrument can generically be referred to as a "probe."

The purpose of spatial registration can be multiple-fold. One benefit is the introduction of the capability to provide three dimensional (3D) models of the investigated objects. These 3D models can include multiple layers of information, such as physical characteristics, as well as other characteristics provided by probe. Another benefit is the determination of the position and orientation of the probe in relationship to the investigated environment. As a result of this, a three dimensional distribution of the quantity measured by the probe can be determined. One dimensional (1D) or two dimensional (2D) distributions can also be determined, if found to be more relevant for a given application.

The methods described herein can allow non-imaging probes, or imaging probes with limited dimensionality, to provide superior three dimensional mapping of an investigated object. Two examples of probes that may benefit from this aspect are: (1) ultrasound scanners for medical investigations, and (2) gamma-probes used for directed search of radioactive hot spots. Other examples of sensing probes are an imaging gamma-ray camera, such as a Compton imager or collimator based imager, an ultrasound scanner or imager, a thermal infrared scanner or imager, a spectroscopic infrared scanner or imager, a ground penetrating radar, and a chemical sensor.

Besides the surgical arts, a field where aspects of the present invention can make an impact is in environmental surveys. Most commonly, the operator of a hand-held surveying sensor should specify a location where a survey is performed in a manual fashion. Environmental surveys would benefit from a method that would conveniently provide the position and orientation of the system in relationship to the investigated objects or to the adjacent environmental objects and keep an automatic log of the surveyed locations. This capability would also allow for an automatic mapping of the investigated features. One particular example of an application that would benefit from such a capability is the measurement of the radioactive dose or radiation field inside structures.

Another field where aspects of the present invention can make an impact is in medical investigative and interventional procedures, as well as telemedicine. "Telemedicine" is broadly defined as the use of telecommunications and information technologies to provide clinical health care remotely. With the recent advances in broadband communications and information technologies, the field of telemedicine has received increased interest due to its potential to reduce healthcare costs and to provide quality healthcare services to populations in isolated areas, or to patients experiencing decreased mobility.

One particular component of telemedicine is remote clinical consultation and diagnosis. Particularly, ultrasound imaging is an attractive tool for clinical evaluations at the point-of-care because of affordability, availability and convenience. These features make ultrasound imaging systems suitable for use at multiple remote locations without the need for an extensive support infrastructure. One obstacle preventing better utilization and larger adoption of ultrasound imaging at the point-of-care is variable operator experience and training. Due to the ultrasound-specific difficulty to find the proper "window" to investigate organs of interest, and because of limited imaging resolution, presence of artifacts and speckles, an ultrasound probe user or operator should have a very specialized training and have extensive experience to properly position the probe and to interpret the image, discriminating fine anatomical features from artifacts and speckle. Operator-dependent accuracy is one of the factors limiting the application of ultrasound in resource-limited settings. To overcome limitations associated with varying levels of training and experience of the ultrasound operator at the point-of-care locations, existing teleconferencing systems allow a remote expert to assist the investigation process by providing verbal instructions to the local ultrasound operator. This process can be cumbersome because of the difficulty of verbally communicate instructions about how to best position the ultrasound probe in a 6-dimensional space (i.e., 3 translations, 3 rotations), with a precision that should be less than 2-3 millimeters translational resolution and less than 2 degrees rotational resolution. This positioning performance is sometimes required in order to capture clinically relevant image planes. Missing the most relevant image plane by a few degrees is enough to miss diagnostically important anatomical features. In order to support the process of positioning the ultrasound probe, several previous approaches involved providing the local operator more information about the anatomy of the investigated areas in a virtual reality 3-D model. The purpose of this approach was to make the local operator more situationally aware of the anatomical structures being investigated. These solutions involve complex augmented reality systems, and they still don't provide a means for a remote trained user to efficiently guide the local operator the best course of action.

In embodiment, different methods and systems that are easier and cheaper to implement than those in the prior art are disclosed. In addition, methods and systems are proposed that allow operators to receive instructions from automated computer guidance systems, previously saved protocols, stereotactic markers, or a combination of these—circumventing the need for assistance from a trained operator.

"Stereotactic ultrasound" is taught herein, as opposed to stereotactic imaging. Stereotactic imaging, especially using CT and MRI, is being used to guide biopsies and other surgical procedures. In its most broad interpretation, stereotactic imaging refers to the capability of an imaging system to identify, label and register anatomical features of interest in 3-D so that follow up medical interventions and investigations can use those same 3-D coordinates to precisely guide medical instruments, or for re-evaluations. A stereotactic ultrasound instrument in accordance with an embodiment can be able to label features of interest in 3-D and register them in respect to anatomical landmarks so that follow-up investigations can easily use those coordinates to re-evaluate various medical conditions.

Another aspect of some embodiments is to provide a user, such as a surgeon or a physician, the capability to track objects in the field of view in respect to each other by using a camera or ranging system placed on another object or on a head-mounted tracking and visualization system. There is no need for using separate tracking cameras or light emitting devices.

Advantages

Among other aspects, some embodiments make use of the latest advances in ranging systems, such as time-of-flight cameras, lidar systems, structured light systems, electromagnetic sender-receiver assemblies, and sonar systems, which allow for a construction of a physical model of the environment and for positioning and tracking of instruments and/or sensors probes in respect to said physical model.

Among other aspects, some embodiments make use of the latest advances in computer vision algorithms which, by using simple and inexpensive visual cameras in conjunction with fiducial markers placed on instruments, on sensor probes, on an investigated object or in the environment, provide positioning and tracking of instruments and/or sensors with respect to the investigated subject or environment, as well as creates a physical model of the investigated subject or environment.

Thus, several advantages of one or more aspects are to provide positioning and orientation of mobile sensors and instruments in the environment in a convenient and inexpensive way. Other advantages of one or more aspects are to provide spatial tracking and logging of the sensors and instruments. Other advantages of one or more aspects are to provide the spatial information necessary to reconstruct the investigated field in one dimension (1-D), 2 dimensions (2-D) or 3 dimensions (3-D). Other advantages of one or more aspects are to provide a modality for a remote user to communicate its choice to a local operator, human or robotic, in what regards the position and orientation of an instrument or sensor in respect to the environment, investigated subjects or other instruments. Other advantages of one or more aspects are to provide capability for stereotactic investigations using ultrasound.

"Stereotactic ultrasound" is a capability to label features of interest identified by an ultrasound scanner and register them in respect to anatomical landmarks so that follow-up investigations can use those coordinates to re-evaluate or treat various medical conditions, or as otherwise known in the art. Other advantages of one or more aspects are to provide computer guidance to operators of sensors and instruments. Other advantages of one or more aspects are to provide an intuitive visualization and graphical interface to local and remote operators when handling sensors and instruments.

Another advantage of some aspects is to allow a user, such as a physician or surgeon, to interact with a computer by moving objects, parts of his or her body without the need to physically touch a human interface while having the possibility at the same time to track the position and orientation of instruments and sensor probes in respect to each other and in respect to the user, and to manipulate medical instruments or sensor probes.

These and other advantages of one or more aspects will become apparent from a consideration of the ensuing description and accompanying drawings.

Figures and Descriptions

FIG. 1 shows a first modality by which spatial registration can be provided to a probe. A ranging device camera RS 102 is mechanically registered to the probe P 101 through a mechanical mount 103. The whole assembly, which is made out of components mechanically registered to the probe 101, can be called a "probe assembly."

Examples of ranging device cameras that can be used are: a time-of-flight camera, a structured light camera, or a lidar scanner.

A computing unit 104, which may or may not be mechanically registered to the probe-ranging device assembly, receives data or electrical signals from the probe and transmits data or electrical signals to the probe through connection 105, in the case when such data or signals are necessary, and from and to the ranging camera 102 through connection 106. Connections 105 and 106 can be wireless or made out of physical cables. The computer 104 receives, processes, and synchronizes data coming from probe and ranging camera and performs further processing.

The investigated subject or environment 107 and 108 are on the left side of the figure. The ranging camera 102 emits a signal which back-scatters off the objects carrying information with regard to distance to those objects. In this figure, the signal emitter is represented by 109, an instantiation of the emitted signal is represented by dashed line 110, the reflection from the object in the direction of the signal receiver is represented by line 111, and the signal receiving sensor of the ranging camera system is represented by 112.

In a "time-of-flight (TOF) ranging camera", the emitted signal is a time modulated or pulsed light that illuminates the parts or the whole field-of-view (FOV) of the receiver 112, preferably emitted by a laser or a Light Emitting Diode (LED), and the signal receiver 112 is a time of flight camera. In the case of a structured light ranging camera, the emitted signal can be infrared (IR), visual or ultraviolet (UV) structured light or modulated light system, and the signal receiver is a IR, visual or UV light camera. In this case, the spatial distance (or lever arm) between the source 109 and receiver 112 can be optimized to provide best range resolution for the intended range of distances. Processing of data from these systems to get 3D models of objects can be performed with stereoscopic algorithms. In the case of a lidar scanner, the emitted signal is a pulsed laser beam, and the receiver is a light sensor able to measure time-of-flight information by direct energy detection or phase sensitive measurements. In the case of a 3D flash lidar, the emitted signal is a pulsed laser beam illuminating the whole field of view (FOV), and the receiver is a specialized light sensing array able to measure time-of-flight information. The computing unit 104 will analyze the range data to determine the relative translation and rotation of a coordinate system 113 associated with the probe 101 in respect to an arbitrary coordinate system 114 associated with the adjacent environment or investigated objects.

The lidar ranging camera, or other time-of-flight camera, can have common optics for the emitter and receiver.

For increased ranging performance, the light source 109 can be made out of multiple physically separated units, and the signal receiver 112 can be made out of multiple receivers physically separated, but mechanically registered to each other. An example when such an implementation can bring benefit is when using a structured light ranging camera. Placing the source of the patterned light between two or more light cameras will insure that the pattern projected by the source will be seen by at least one camera. Moreover, superior ranging precision can be obtained by using the stereoscopic-like information provided by any combination of multiple such cameras.

For increased tracking performance, the ranging camera based tracking system can be combined with other tracking systems, such as an inertial measurement unit (IMU), computer vision system, or ultrasound or electromagnetic ranging systems.

Another example of merging various ranging and tracking systems is when a lidar system is used jointly with an IMU system for spatial registration. The operator will scan the environment with the lidar, and the IMU will provide dead reckoning information. Combining the two data, spatial registration of the probe in respect to the adjacent environment can be obtained.

Figure 2:
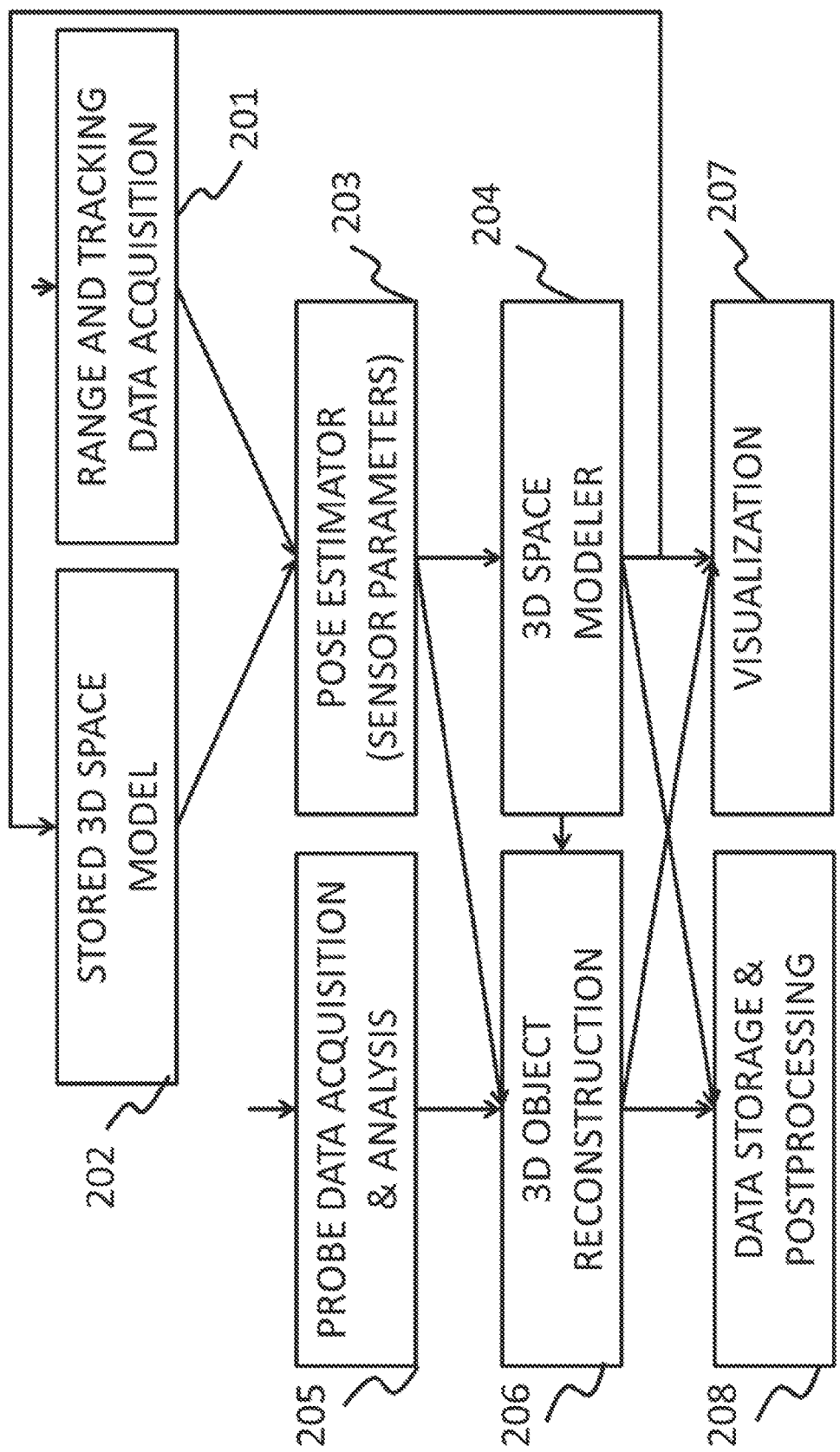
FIG. 2 is a flowchart of data processing steps using a generic ranging and tracking system mechanically registered to the probe in accordance with an embodiment.

FIG. 2 shows an example of how the range data can be used to provide the relative position and orientation of the probe in respect to the investigated objects and adjacent environment, and how that can be used to build more complete models of the features mapped by the probe in the case when the probe is a sensor.

The data coming from the ranging and tracking camera 102 (see FIG. 1) are fed into a data acquisition system 201. In order to obtain tracking information from range data, a previously stored 3D space model 202 is used as a reference. This model represents the outline of the objects in the environment and could have been created during a previous measurement session, or from computer generated models such as computer aided design (CAD) models, or during the same investigative session, from previously recorded range scans. If no previous 3D models exist, a blank state can be assumed. For each moment of time, the range and tracking data is merged with the pre-existing 3D space model 202 by a pose estimator module 203 that matches the current range data with the pre-existing 3D model. Because the current range data may only partially overlap with the pre-existing 3D model, conditions for what fraction of the scanned surfaces should overlap will depend on the application. From this process, the pose of the ranging sensor in respect to the 3D model of the environment is determined. In support of the process, other tracking sensors, such as IMUs, can be used to constrain the search for the best fit, and the best pose.

The result of this process will be an extension of the pre-existing 3-D model with the current range data. This is done as part of step 204. The resulting model can be used as a pre-existing 3-D model 202 for the next frames. At the same time, the data coming from the sensor probe 101 (see FIG. 1) is fed into the probe data acquisition and analysis module 205. After the probe data is synchronized with the tracking (or pose estimate) data, an Object Structure Reconstruction module 206 is used to build a volumetric distribution of the features mapped by the probe.

At step 206, at each moment in time, the probe data is associated with the spatial position and orientation of the probe provided by the machine vision system to create spatially registered data. This allows the system to track the amplitude of the probe data as function of the position and orientation of the probe in space, allowing for a reconstruction of the spatial distribution of the investigated field or even the source term.

The "source term" is the source of the amplitude values measured by the probe. For example, for a gamma-ray probe, the source term is the gamma-ray source, which most commonly is a radioactive tracer; for an ultrasound sensor, the source term is the sound scattering and reflecting properties of the investigated material. For a chemical sensor, the source term is the source of a chemical element or molecule of interest.

The "investigated field" mentioned above can be the radioactive dose, if a radiation detector or a radiation dosimeter is used. It can be chemical concentrations, if a chemical sensor is used, etc.

In order to perform the reconstruction of the source term distribution, various algorithms that resolve inverse problems can be used. In this way, a higher dimensionality model (2-D or 3-D) of the features mapped by the probe is obtained. The information about the probe position and orientation can be also used along with the output of the 3-D space modeler 204, the 3-D contour of the investigated objects and/or environment, to constrain the solution of the distribution of field mapped by the probe, for better visualization and for spatial registration of the investigated field in respect to the environment.

A visualization module 207 may be used to visualize the various models for user inspection and analysis. The visualization module may also include a user interface capability which allows the user to navigate the models, change visualization options, change system settings, and obtain supplementary information about the various components of the scene. Examples of visualization modules are: a computer screen, a touch screen, augmented reality devices or goggles, projectors, head mounted displays. All or parts of the ensuing models and data can then be saved for follow up inspections or further processing in module 208.

Figure 3:
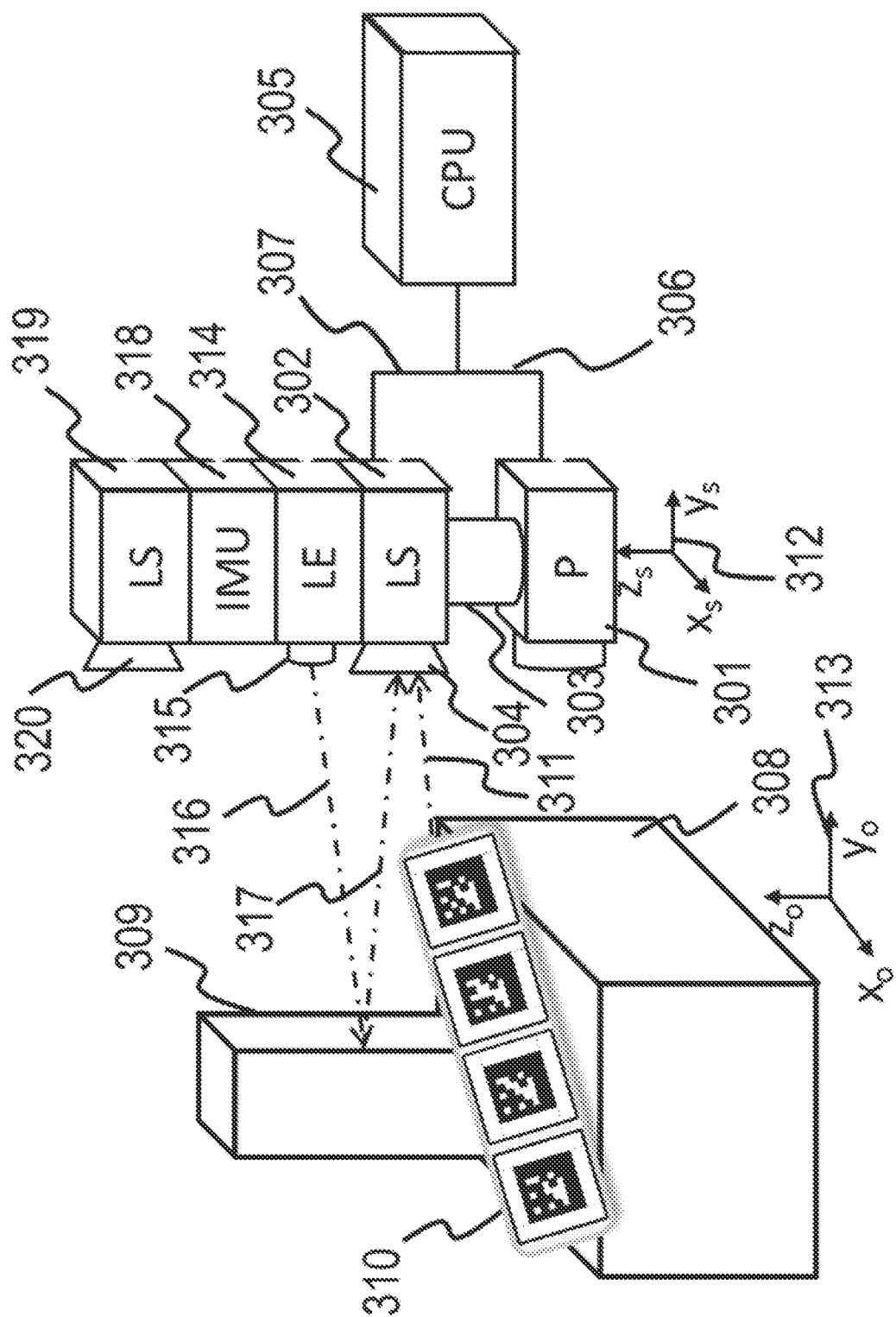
FIG. 3. illustrates tracking and spatial registration of probes with respect to an investigated environment using various optical methods in accordance with an embodiment.

FIG. 3 shows another approach to provide the position and orientation of the probe 301 in respect to the investigated objects or adjacent environment. In this case, probe tracking information and the outline of the 3-D model of objects are obtained by using mostly passive light sensing components. A light sensing device 302, such as a high definition video camera, is mechanically registered to the probe 301 through a mechanical connection 303. The whole assembly made out of components mechanically registered to the probe 301 will be called "probe assembly."

The opening for light collection is represented by 304. Similar to the embodiment of FIG. 1, a computing unit 305, which may or may not be mechanically registered to the probe-ranging camera assembly, receives data from the probe and transmits data to the probe through connection 306, in the case when such data is available, and from and to the light sensing system 302 through connection 307. Connections 306 and 307 can be wireless, or can be made out of physical cables.

The computer 305, receives and synchronizes the data coming from the probe and ranging camera and performs further processing. The investigated subject or environment 308 and 309 are at the left side of the figure. A fiducial object 310 with well-defined measurements may be mechanically registered to the investigated object to provide a reference system associated to the investigated object, to provide scale to the scene, and to provide features or landmarks that are easy to identify and to track.

Figure 4B:
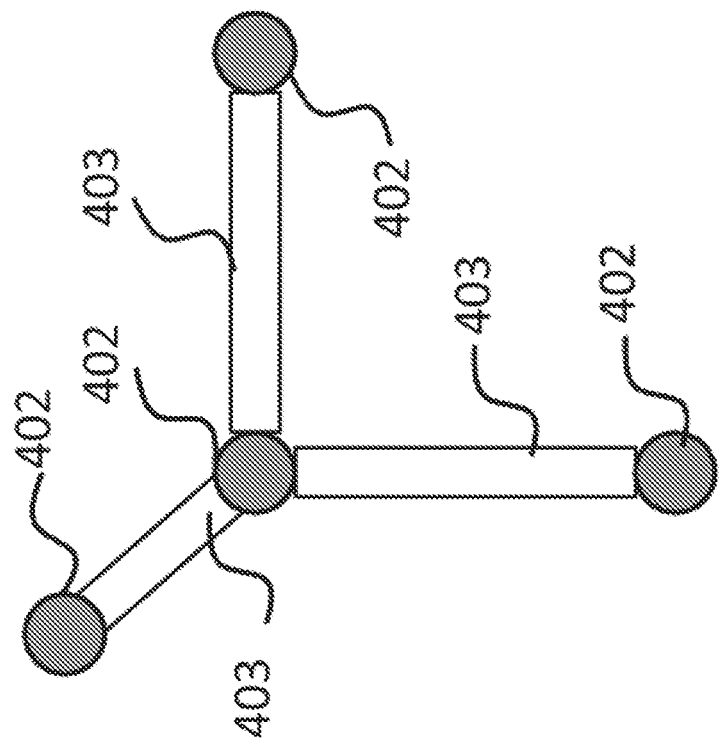
FIG. 4B illustrates an alternative fiducial object in accordance with an embodiment.
Figure 4A:
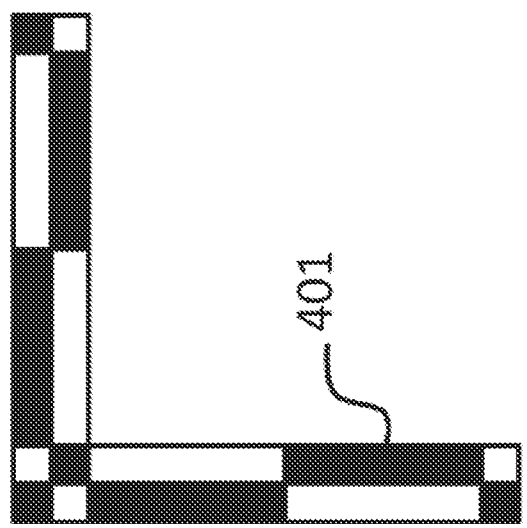
FIG. 4A illustrates an example fiducial object in accordance with an embodiment.
Figure 5:
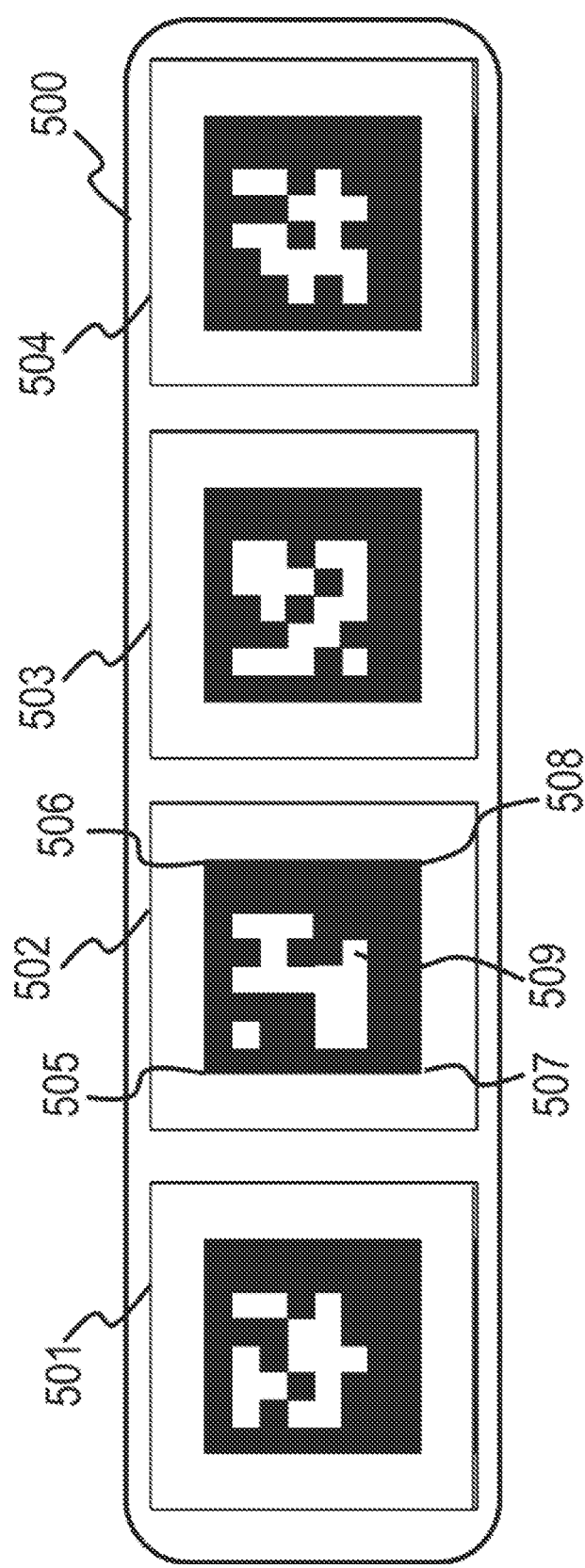
FIG. 5 illustrates a tape-like piece-wise rigid fiducial object in accordance with an embodiment.

Various examples of fiducial objects are presented in FIGS. 4 and 5. Ambient light can be used to illuminate the fiducial marker 310, or the fiducial marker could comprise active light sources, such as IR or visible LEDs. A light source connected to the tracking system can be used to illuminate the scene.

The light scattered or emitted by the fiducial marker is represented by the dashed-arrow 311 (FIG. 3). A perspective n-point algorithm can be used on the computer 305 to process the apparent shape of the fiducial as seen by the light sensor 302 to determine the relative translation and rotation of a coordinate system 312 associated with the probe 301 in respect to a coordinate system 313 associated with the fiducial marker. Since the fiducial marker is mechanically registered to the investigated object, the coordinate system 313 can be interpreted as being attached to the investigated objects.

Additionally, the probe assembly may comprise a light source 314 to more easily highlight the fiducial object 310 or marker, as well as the investigated objects. The light output opening 315 is on light source 314. An instantiation of the emitted light represented by dashed arrow 316 is shown falling on the object 309, and a scattered light photon going towards the light sensor 302 is represented by the dashed line 317. Similar rays of light will fall on all objects in the field of view of the system, including on the whole or parts of the fiducial object 310.

Structure from motion algorithms can be implemented on the computer 305 to construct the 3-D model of the outline of investigated objects and adjacent environment, when the probe system is moved in space. To increase probe tracking performance, an IMU 318 can be mechanically registered to the probe assembly.

Figure 7:
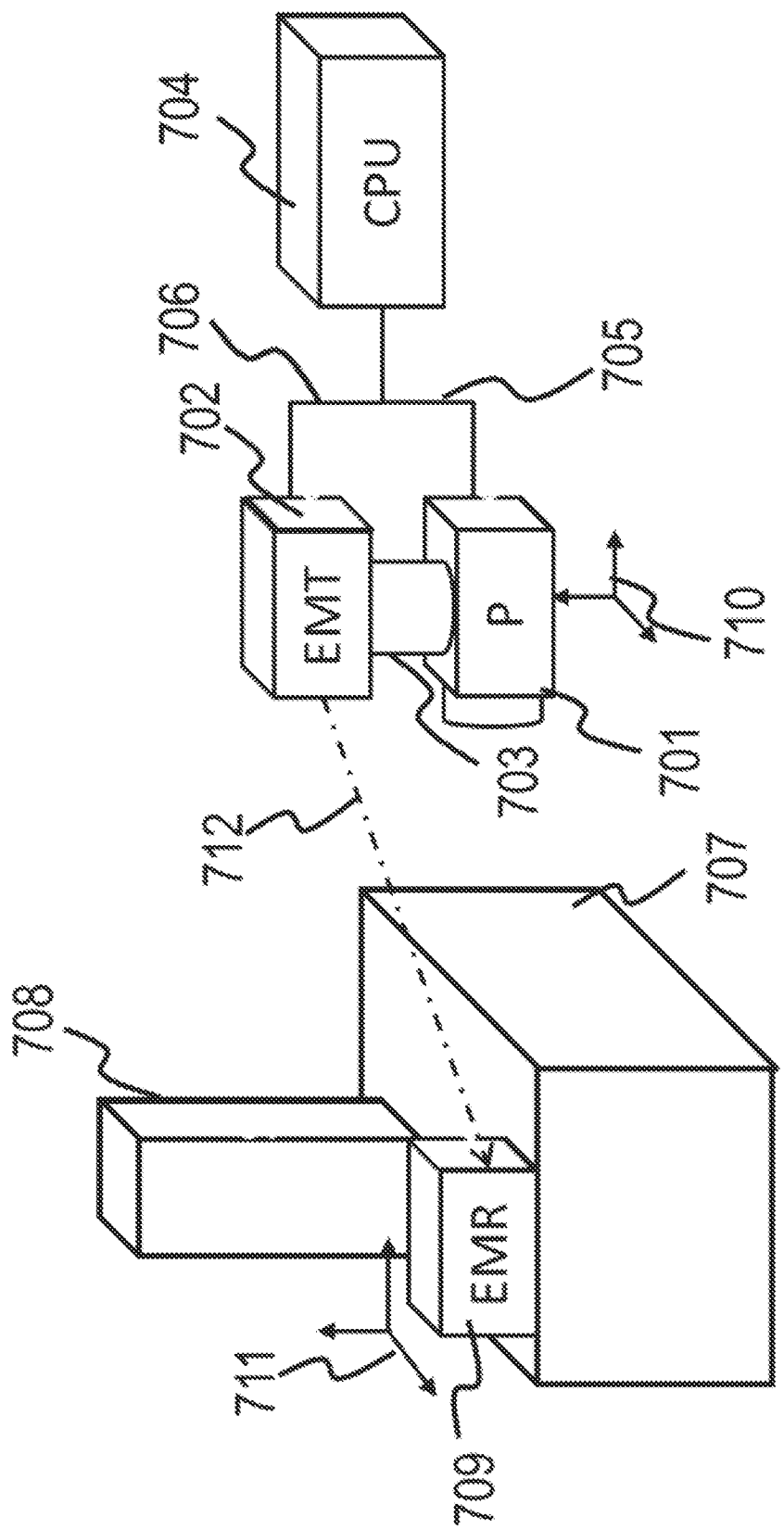
FIG. 7 illustrates tracking and spatial registration of a probe in respect to an investigated environment using an electromagnetic ranging system mechanically registered to the probe in accordance with an embodiment.
Figure 8:
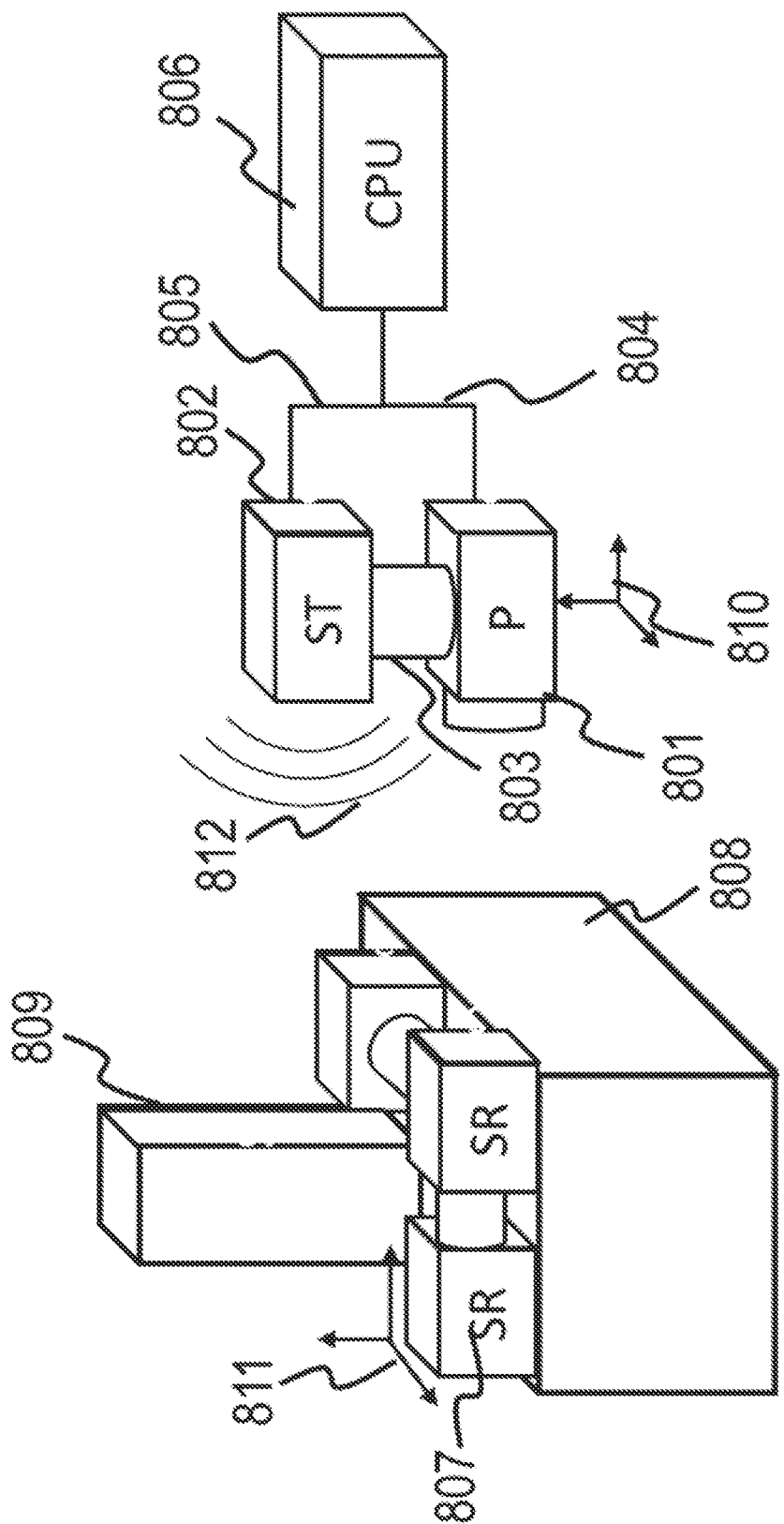
FIG. 8 illustrates tracking and spatial registration of a probe in respect to an investigated environment using an ultrasound ranging system mechanically registered to the probe in accordance with an embodiment.

For spatial registration redundancy, the fiducial objects 310 can also comprise other spatial registration elements, such as electromagnetic receivers as 709 in FIG. 7 or ultrasound receivers as 807 in FIG. 8. These receivers can be used in conjunction with electromagnetic emitters 702 in FIG. 7 7 and ultrasound emitters 802 in FIG. 8, respectively.

Additionally, the light sensing system can comprise an assembly of two or more light sensing devices, such as a stereoscopic system made of at least two video cameras that have an overlapping field of view. One advantage of using an assembly of light sensing devices is an increased field of view. Another advantage of a stereoscopic system, in particular, is that for the 3D modeler analysis step described below (in step 604 of FIG. 6), to be implemented on computer 305, the scale of the investigated scene will be apparent from matching the frames taken simultaneously from the multiple cameras, whose relative positions and orientations can be known with high precision. Also, in this arrangement no movement of the system is necessary to construct the 3D model of the investigated object.

In this figure only two light sensing devices are shown. The second light sensing device 319 is shown mechanically registered to the probe assembly with a precise relative position and orientation from light sensing device 302. Stereoscopic algorithms can analyze the sensing data from the two light sensing devices to calculate the position and orientation of the probe in respect to the investigated objects and to increase precision in the determination of the 3-D model of the outline of investigated objects and adjacent environment. The opening of the light sensing device 319 for light collection is represented by 320. More than two units can be used in order to get more complete information from the same FOV or to increase the overall instrument FOV.

Additionally, a similar computer vision camera system can be mounted on other sensors and instruments that can be used simultaneously with probe 301. The spatial tracking data from all these elements can be combined to create a common spatial model comprising instruments and investigated fields. An example of an application using this setup is the intraoperative use of an ultrasound scanner along other surgical instruments. The ultrasound scanner and the surgical instruments can each of them be fitted with computer vision camera systems, or some of the components can comprise elements which act as fiducial elements.

Examples of light sensing devices are charge-coupled devices (CCD) or complementary metal-oxide semiconductor (CMOS) sensors. Embodiments using this method can include cameras that are sensitive to visible and/or infrared radiation. As such, the light source may emit in visible or IR. The camera(s) can also be a light-field camera, also called a plenoptic camera, a hyperspectral camera, or a compressive sensing camera.

One purpose of the fiducial object 310 is to help the computer vision system better determine the scale of the whole scene, to unambiguously position the probe in the scene, and to provide a landmark for 3-D modeling of the object outline. A fiducial object can be referred to as a "reference object." Alternatively to a fiducial object, a fiducial marker, such as a label with clearly distinguishable features can be placed on various objects in the environment.

The data stream (or video stream) coming from the light sensing device (or camera) is analyzed to identify the fiducial object in the field of view. By analyzing the apparent form of the fiducial object, the position and orientation of the probe in respect to the fiducial object is obtained, and from that, the position and orientation of the probe in respect to the investigated object.

FIGS. 4A and 4B illustrates fiducial objects in accordance with embodiments. In FIG. 4A, the fiducial object 401 is in a bar shape in a straight angled elbow that is painted in a pattern of contrasting colors. Alternatively, painted reflective material can be used to improve visibility. In FIG. 4B, the fiducial object includes a frame 403 that supports four spherical objects 402. These spherical objects can be either devices actively emitting light, such as light emitting diodes (LEDs), or can be objects made from a material that is efficient at diffusely reflecting the IR or visual radiation.

A particular fiducial object that may be suitable to provide fiducial marking to a large surface area are piece-wise rigid bands. Each rigid piece can have a pattern similar to the QR or AR codes, but optimized for pose estimate determination. An example of such a fiduciary is shown in FIG. 5. The substrate tape 500 of the fiducial object can be laid on an investigated object (such a as patient in medical investigations) in an area close enough to the area to be investigated. This substrate can be made from a flexible material such as rubber, elastomers, such as silicone, polyurethane and latex, or other material flexible enough to follow the layout of the object.

The backing that will be towards the patient can be made of the same material or a different material that is adhesive enough to not allow the fiducial to slide easily across the skin or cloths of the patient. The figure shows a fiducial in the form of the letter I. Other arrangements are possible, such as a in a form of a L, T, V, U, or other pattern, the choice of which can depend on the particular area to be investigated.

One or more rigid pieces can be mounted on this form. Several such fiducials can be used concurrently. These rigid pieces are shown in the figure by 501, 502, 503 and 504. On each of these pieces, a pattern can show distinguishable features that allow the machine vision system to get a physical scale of the environment, get a pose estimate, and uniquely identify the type of fiducial, and the place of the piece within the whole fiducial. Some of these features are indicated for the 502 piece. Corners 505, 506, 507, and 508 made by the black squares in the four corners of the 502 piece with the central large square will provide most reliable information to the machine vision analysis to determine scale of the environment and camera pose. The middle pattern 509 will comprise a distinct binary code that will uniquely identify the corners 505, 506, 507, and 508, as well as the fiducial type, index, and the relative position of the pattern within the whole fiducial.

Figure 6:
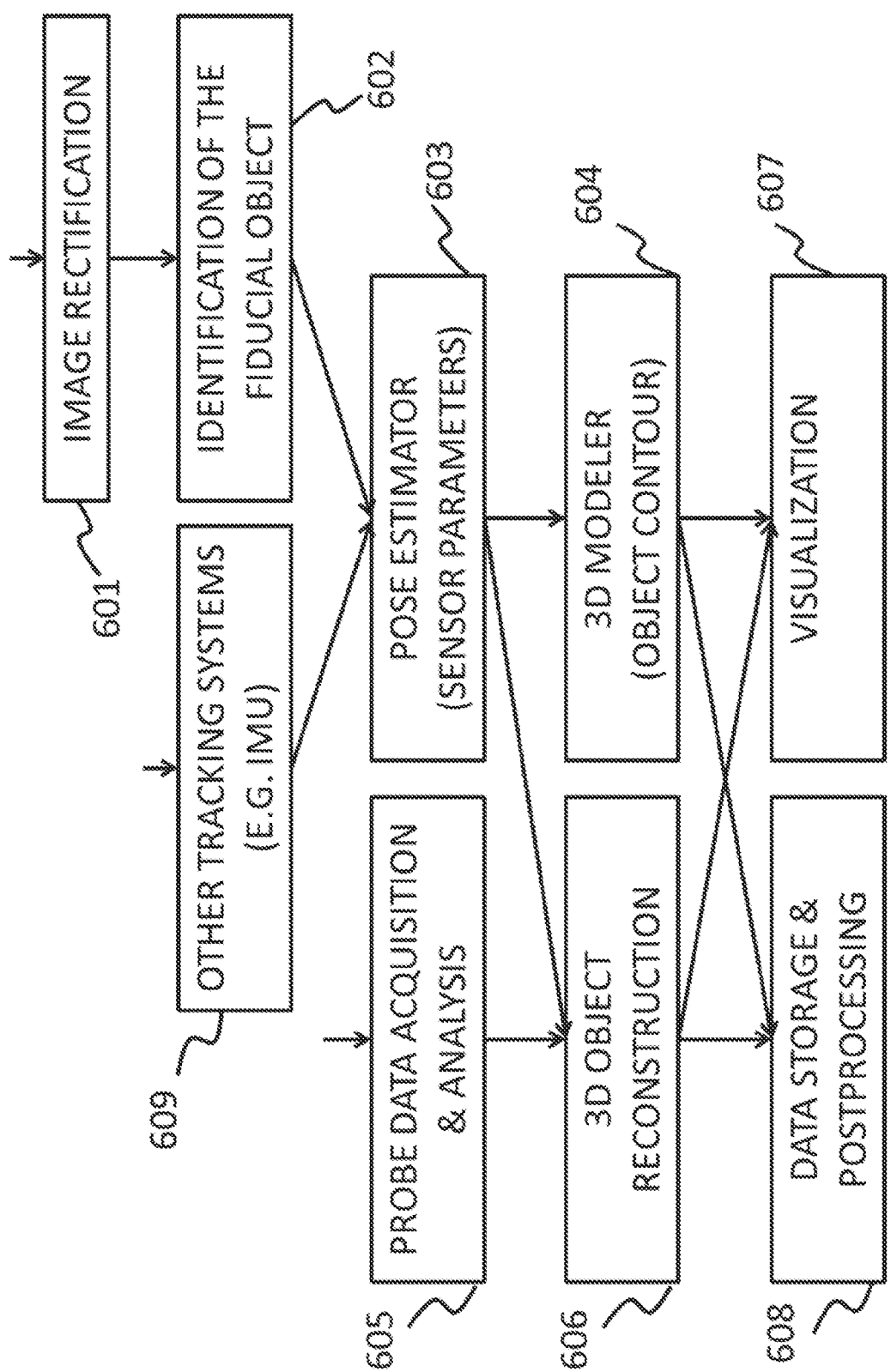
FIG. 6 is a flowchart of data processing steps using a generic machine vision system mechanically registered to the probe in accordance with an embodiment.

A more detailed example of an implementation of the data analysis chain when using passive light sensing devices is shown in FIG. 6. In the embodiment, there are two main streams of data, one coming from the probe, when applicable, the other coming from the light sensing devices (or computer vision cameras). The data coming from the computer vision cameras is analyzed by a computer vision analysis chain.

In most implementations, the image frames have to be rectified to correct for the distortion of the optics and to account for the response of the camera to points at various positions in space. Therefore, an image rectification 601 analysis step may be used to correct the position of the pixels in the frame using a pre-measured calibration matrix. The calibration matrix is obtained by taking various pictures of known 3D objects or 2D planes positioned at different angles and positions in the field of view. The calibration and rectification methods are commonly known in the field.

The second computer vision analysis step 602 identifies the fiducial object or fiducial marker in the field of view, and uses its apparent shape to determine the position and orientation of the computer vision camera in respect to that fiducial object in the following pose estimator step 603. Since the camera is mechanically registered to the probe, a position and orientation of the probe is determined by simple transformations. In the case in which a fiducial object is not used, various features of the investigated objects or in the environment can be used as reference points.

Whereas when fiducial markers are used, the movement of the computer vision system in respect to the investigated objects may not be necessary; when fiducials are not used, the algorithms under this step 603 may require the observation of the investigated object by the computer vision camera or cameras from various angles.

A 3-D modeler (or dense machine vision) step 604 may also be used to determine object parameters, such as 3-D models of the contours of the objects being investigated or from the adjacent environment. Building the contour 3-D model reliably using dense machine vision 604 algorithms may also require the observation of the investigated object by the computer vision camera or cameras from various angles. Various features in the field of view are tracked in time across frames taken successively as the camera is moved, and a full 3 dimensional position of the object features is calculated, as in step 604. This process uses computer vision algorithms that create 3-D structure from video.

Structure from motion algorithms can be used to build the 3-D contour of the investigated object, environment or patient. This contour 3-D model can be integrated into the common virtual 3-D model of the setup. The registration of the probe within the virtual 3-D model can be obtained by analyzing the apparent shape of the fiduciary object, as seen from the computer vision camera on a computer device.

The problem of estimating camera pose from observing pre-defined fiduciary points is known in the computer vision field as the perspective-n-point problem (PnP).

A linear solution that requires four points for a unique solution was published in Ansar A, Daniilidis K., "Linear pose estimation from points or lines," *Pattern Analysis and Machine Intelligence*, IEEE Transactions on 2003; 25:578-89, which is hereby incorporated by reference.

More recently, Lepetit V, Moreno-Noguer F, Fua P. "An Accurate O (n) Solution to the PnP Problem," *International Journal of Computer Vision*, 2009; 81:155-66, which is herein incorporated by reference, presented an O(n) solution for n>=4.

For a strictly 3 point solution, Xiao-Shan G, Xiao-Rong H, Jianliang T, Hang-Fei C., "Complete solution classification for the perspective-three-point problem," *Pattern Analysis and Machine Intelligence*, IEEE Transactions on. 2003; 25:930-43, which is hereby incorporated by reference, describes another approach suitable for this applications.

Present embodiments using computer vision systems and inertial measurement units for probe tracking eliminate shortcomings of other approaches for tracking, such as the need for external, bulky optical trackers or magnetic emitters, the need to maintain a long line of sight, or the need to maintain a "clean" magnetic environment. One of the problems associated with determining structure from video is the determination of the scale of the object. To resolve this problem, the fiducial object or marker, which is of known shape and dimensions, can be used to determine the right scale, providing exact object dimensions. Examples of fiducial objects are described above and in FIGS. 4A-5. The fiducial object can also be used to define the reference system for the whole scene. If fiducial objects or markers are not available, the proper scale can be determined by using either a stereoscopic computer vision system, a lidar system, a ranging camera, an Inertial Navigation Unit (INU), or a combination of these, each of which registered to the probe or integrated into the probe.

The data coming from the probe, when available, is read-out and adjusted (see step 605) to be used in the 3D Object Structure Reconstruction analysis step 606. The information about the probe position can be associated with the probe data coming from the probe data acquisition and analysis step 405 to create spatially registered data.

This spatially registered data can be used to build a 2-D or 3-D distribution of the features mapped by the probe. This is done under the 3D object structure reconstruction process 606. From here on, steps 606, 607 and 608 are similar in function with step 206, 207 and 208 of FIG. 2, respectively, and their description is appropriate here.

In an alternative mode of operation, no fiducial objects or markers are used. In such a case, or when the fiducial objects or markers are not in the field of view, step 602 can be skipped, and the data from step 601 will go directly to step 603. This operation mode may be more common in broad area surveillance and mapping applications, where the use of fiducial objects or markers may not always be practical. In this case, an estimate of the 3D position and orientation of the camera is obtained by tracking features and highlights associated with various objects in the field of view in subsequent image frames. By triangulation, the distance to these highlights can be calculated, and from that, the spatial registration of the sensor in respect to these highlights is determined. At the same time, the 3D model of the whole scene can be built. However, if there is no reference (or fiducials) in the scene to indicate the absolute scale of the scene, the determined dimensions have relative values.

To get an estimate of the absolute values in this case, other positioning systems can be combined with the computer vision system, such as an inertial measurement unit (IMU), a laser based range finder (LIDAR), or any combination of these. Even though tracking of positions and orientations using IMU dead reckoning may lead to drifts over its use, by combining the information from dead reckoning with the computer vision-based spatial registration, improved positioning can be achieved.

A lidar system using a laser beam (or several beams) can be used to get the absolute distance to objects in the environment for selected points. By identifying the points where the laser beam hits an object in the camera frames, and by using the absolute distance values provided by the lidar system, the absolute scale of the scene can be deduced. The figure includes the implementation in which the tracking and spatial registration system uses an external tracking or ranging camera, such as an IMU, a LIDAR, or other system.

If other tracking systems are used synchronously, such as IMUs, or ranging cameras, their corresponding data stream is read out in step 609, and merged with the camera data in step 603 to improve pose estimate performance by using multi-sensor filters, such as Kalman filters. For example, in step 609 data from an IMU can be used for dead-reckoning or the range data from a LIDAR is used for laser ranging.

In yet another implementation, a fiduciary marker or object can be mechanically registered to the probe, and a computer vision tracking system or a ranging camera external to the probe can be used to observe the spatial field where the probe will be used. The data from the external tracking and ranging camera can be read-out by a computer unit. For increased performance, another tracking system, such as an IMU, registered to the probe can be used. The data from this tracking system can be read-out by the same computing unit that reads the external tracking and ranging camera.

FIG. 7 shows a tracking system that uses electromagnetic waves for ranging. An example of electromagnetic waves is magnetic fields. Electromagnetic pulses, including magnetic fields, can be used but in which the active electromagnetic elements are placed inside the instruments and sensor probes, and are used as active elements emitting electromagnetic fields. The electromagnetic sensors inside reference objects are used as passive elements. An advantage to this mode of operation is that the amplification electronics required to amplify the signal detected by the passive electromagnetic sensors can be placed very close to the sensors, eliminating the need for long wires between the sensors and amplifiers, reducing noise pick-up.

Examples of electromagnetic sensors are magnetic sensors, such as coils. Since the magnetic sensors are directional, a set of three magnetic sensors oriented orthogonal to each other will be enough to provide the position and orientation of the probe in 3D in respect to the reference object, if a set of 3 orthogonal active magnetic elements are placed in the probe, and emit magnetic pulses.

An electromagnetic transmitter 702 is mechanically registered to the probe 701 through the mechanical mount 703. Similarly to FIGS. 1 and 3, a computing unit 704, which may or may not be mounted to the probe-ranging device assembly, may send and receive data from the probe through connection 705, in the case when such data is available, and from and to the electromagnetic transmitter 702 through connection 706. Connections 705 and 706 can be wireless, or can be made out of physical cables.

The computer 704, receives and synchronizes the signals and data sent to and coming from the probe 701 and electromagnetic transmitter 702, and performs further processing. The investigated subject or environment is abstractly represented by the rectangular boxes 707 and 708. An electromagnetic receiver 709 is set on or mounted to an investigated object or instrument in relation to which tracking of the probe 701 needs to be done.

By analyzing the intensity and/or the phase of the electromagnetic signal transmitted by the transmitter 702, relative position and orientation of the coordinate system 710 associated with the transmitter 702 in respect to a coordinate system 711 associated with the receiver 709 can be obtained, hence the relative position of the probe assembly.

The signal received by 709 is transformed into data that can be transmitted to a computer, such as 704 through cables or wirelessly. A "type of signal" that can be used for such a positioning method is a magnetic signal. In the present embodiment the transmitter is mechanically registered to the probe.

Alternatively or additionally, unit 709 can be used as an electromagnetic emitter and unit 702 can be used as an electromagnetic transmitter. In this case, the emitter 709 will emit electromagnetic fields that will be detected by the electromagnetic sensors 702 mechanically registered to the probes.

In another implementation, multiple signal receiving elements can be used for better estimation of the relative position and orientation, or for getting the tracking information for multiple components, objects, instruments of sensors.

FIG. 8 shows another tracking system that uses assemblies of ultrasound transmitters and receivers. The setup has a few elements similar to the embodiments of FIG. 1, 3 or 7. In this embodiment, an ultrasound transmitter 802 is mechanically registered to the probe 801 through a mechanical connection 803. Lines 804 and 805 are data connections from the probe 801 and transmitter 802, respectively, to a computer 806. The ultrasound receiving system 807 is an assembly of multiple individual receivers mechanically registered to each other placed on an object 808.

In this figure, three such receivers are shown. Objects from the environment 808 and 809 are on the left side of the figure. The coordinate system associated with the probe is 810; the coordinate system associated with the receiver is 811. The transmitter emits ultrasound pulses 812 of frequencies preferably above human hearing range, but low enough to insure transmission through air. The received signals can be transformed into data and transferred to the computer 806 wirelessly or using cables. By measuring the time of flight and intensity of the ultrasound waves for each individual receiver, the position and orientation of coordinate system 810 can be found in respect to coordinate system 811. The calculation can be done on the computer 806 or on a processor integrated with the receiving system 807.

Thus, since the proposed methods of merging spatial registration systems with various sensor and instrument probes provide tracking and logging of the said probes with high precision in an efficient, inexpensive and compact package, another one of several advantages are to provide the spatial information necessary to reconstruct the investigated field in one dimension (1D), 2 dimensions (2D) or 3 dimensions (3D).

An application where some aspects of the present invention can significantly make an impact is in the detection of the sentinel lymph nodes using gamma-ray probes. Gamma-ray probes are currently used for navigated sentinel lymph node dissection in intra-operative applications. It is of interest to locate and extirpate the lymph nodes (also known as sentinel lymph nodes) that receive the lymph draining from the general area of the cancerous tumor because these are the first places where cancer cells can propagate.

Typically in a lymph node detection application, a solution containing a radioactive tracer, such as Tc-99m, is injected inside the tissue near the tumor so that it will drain into the sentinel lymph nodes. Subsequently, a collimated gamma-ray detector is used by a surgeon to determine the position of the sentinel lymph nodes by monitoring the count rates detected by said collimated radiation detector as the surgeon moves the gamma-probe around the relevant body areas. A tracking and spatial registration system mechanically registered to a gamma-ray probe can provide the spatial tracking of the gamma-ray probe as the probe is moved around the investigated human body. This will allow the surgeon to get a full three-dimensional distribution of the injected Tc-99m inside the patient and to have that distribution spatially registered to the body of the patient and/or the gamma probe itself and/or other instruments.

Figure 9:
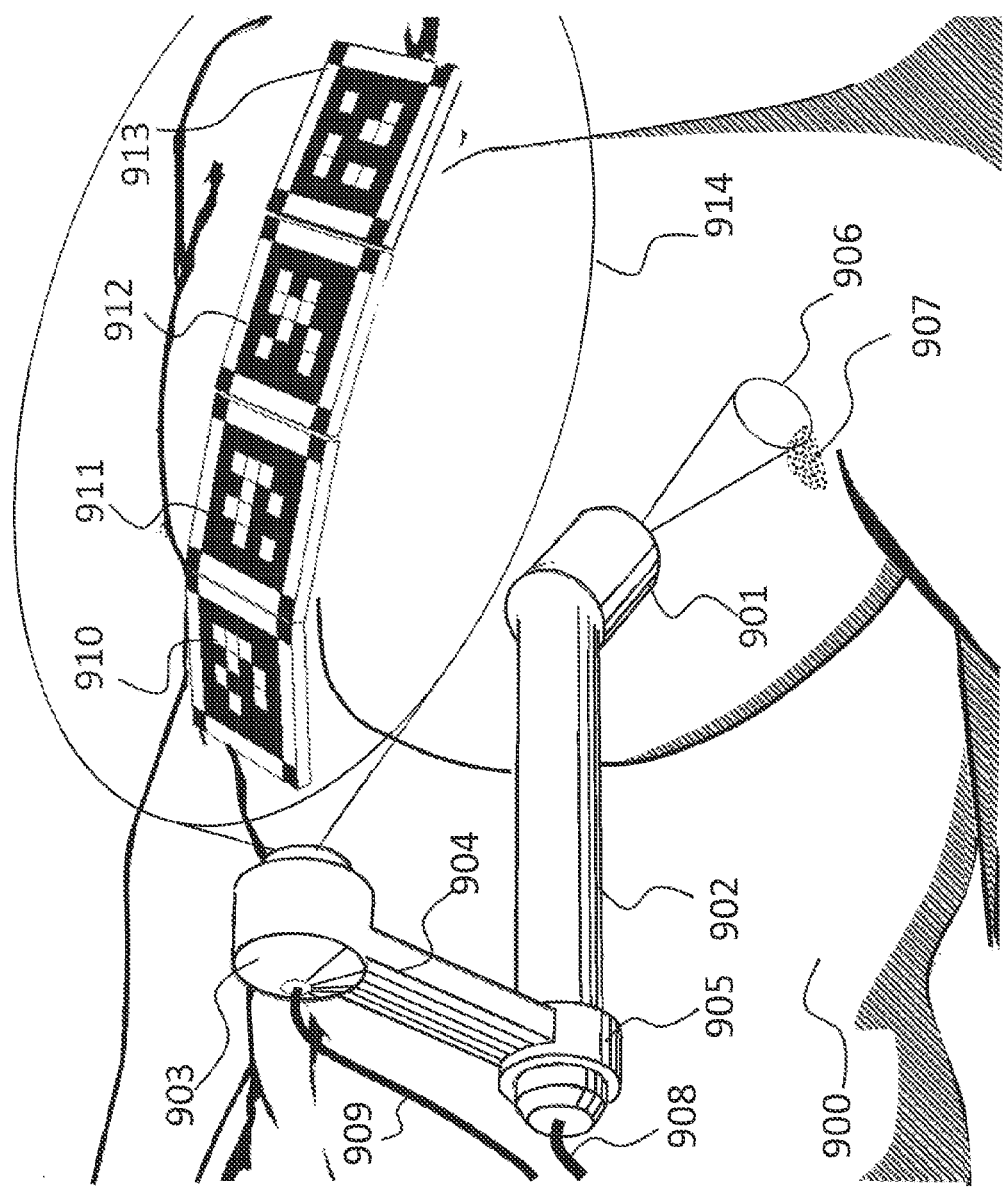
FIG. 9 illustrates a tracking enabled gamma-ray probe used to detect sentinel lymph nodes in accordance with an embodiment.

FIG. 9 shows an example of an embodiment that accurately and reliably determines the position of the lymph nodes. A patient is represented by the torso shape 900. A gamma-ray probe is made out of a probe head 901, handle 902 and tracking system 903 connected to the probe handle by an arm 904. The gamma probe assembly can be made out of an integrated structure, or the tracking system can be mounted on the gamma-probe handle using a mounting mechanism 905 such as a bracketed structure. The mechanical structure will insure high mechanical registration between the gamma-ray probe head 901 and the tracking system 903.

The gamma-ray probe head 901 comprises a gamma-ray detector, such as a semiconductor detector or scintillator, surrounded by a collimator that allows gamma-rays from a limited field of view to enter the detector. The field of view of the gamma-ray detector is represented by the cone 906. A distribution of gamma-ray radioactive tracer, such as Tc-99m is represented by the patch 907, which is inside the body of the patient 900.

Streams of digital data or analog signals coming from the gamma-ray detector are read out by a read-out and processing unit through a cable 908. This cable can contain wires that also read out the tracking system 903. Alternatively, the tracking system can be read-out through a separate cable 909. The data coming from the tracking unit and from the gamma-ray detector will be synchronized inside a read-out processing unit. The tracking system can be any of the tracking modalities presented above.

In the present embodiment, the tracking system is a machine vision system comprising 3 main elements: (1) a light sensing device 903, such as a video camera, that is appended with high mechanical registration precision to the handle of the gamma probe 902; (2) an active or passive fiducial object, or objects 910, 911, 912, 913 that can be mounted or laid on the patient 900 and that contains active or passive features easily identifiable by the camera 903 (whereas active features can be light emitting elements, passive features can be painted forms); and (3) a data acquisition and processing module, such as a computer that reads the video stream and integrates it with the information obtained from the gamma probe.

The field of view for the computer vision camera 903 is represented generically by the opening angle 914. A spatial registration system similar to 903 can be mechanically registered to other surgical instruments to allow tracking their position in space in respect to the same fiducial objects 910, 911, 912, and 913. This spatial registration system will be read out by the same computer that reads the data and analyses the tracking information provided by 903. This will allow real-time positioning in a common virtual model of all elements of interest, such as all relevant instruments, the gamma-ray probe, the investigated patient, the map of the radioactive hot spots indicating sentinel lymph nodes and potential cancerous tissue, etc.

Alternatively, a ranging system as described in FIGS. 1, 7 and 8, can be mechanically registered to the gamma-ray probe and other instruments to provide gamma-probe tracking for the lymph node detection application.

There are several advantages associated to the present lymph node detection approach: better sensitivity, better location, lower radiation dose, faster process, and a shorter surgical procedure.

Another important application of the present methods is in medical sonography. Tracking and spatial registration systems, as presented above, mechanically registered to an ultrasound scanner can provide spatial tracking of the ultrasound probe as the probe head is moved around an investigated object, such as a human body. An improved ultrasound investigation will benefit especially from using ranging systems or passive light sensing systems used with fiducial objects placed on the investigated body, or mounted to a fixed structure adjacent to it. This spatial tracking will allow an algorithm running on a computer to merge the 2-dimensional images created by the ultra-sound scanner into a 3-dimensional model. This will effectively transform inexpensive 2D ultra-sound scanners into 3D scanners. This application can be referred to as "freehand 3D ultrasound imaging." Spatial tracking of the ultrasound scanner using a tracking system mechanically registered to the ultrasound probe has other multiple advantages compared to other tracking systems known in the field:

It uses inexpensive ranging, IMUs or camera systems; it is compact, easily transportable, and the setup of the assembly is very fast.

The delivered positioning and orientation precision is not largely affected by the presence of metallic objects of other external magnetic fields as the magnetic trackers.

A line of sight needs to be maintained from the computer vision camera to the fiducial object for best performance, or from the ranging systems to the investigated and adjacent objects, but this line of sight is very short as compared to CMM-based systems, and therefore, much easier to maintain.

When the line of sight to the fiducial or to the patient is broken, position and orientation can still be determined from using pose estimate algorithms by observing other adjacent objects. Additionally, IMUs, ultrasound speckle decorrelation tracking, ultrasound ranging systems and electromagnetic ranging systems can be used for redundancy. A "merging" algorithm can be used to integrate the information provided by all these tracking elements.

These and other benefits give spatial registration systems mechanically registered to the ultrasound probe a clear advantage for freehand ultrasound imaging. Moreover, this implementation will also allow ultrasound scanners with 3D transducers to have larger effective field of views by overlapping multiple 3D scans taken at various angles and positions. Furthermore, it will also allow better use of the 2D images by spatially registering them.

Another advantage of this approach is that by keeping track of the superposition of the scans and observing the same structures from various angles and positions, it is possible to identify and correct ultrasound specific artifacts, such as reverberations, refractions, ghost images, "comets", etc.

Yet, another advantage of this approach is that in the intraoperative use of ultrasound to navigate medical instruments, the user, or the operator will have much more confidence in the ultrasound models, since the organs and structures will be spatially much better defined, with much reduced artifacts. The surgeon will be able to follow in real time, in a common virtual model, all elements of interest, such as the medical instruments, the ultrasound scanner, the investigated body, the 3D ultrasound model of the organs, and potentially, other pre-operative models. Moreover, image segmentation algorithms can be used in the process of merging the 2D ultra-sound images into the 3D ultra-sound model and to delimitate various features in the 3D model, such as organs, tissues, etc. Computer expert systems can also be employed to identify anomalies and other specific features that are clinically relevant.

Among other aspects, the present invention also describes an inexpensive and efficient way to create a virtual reality model of an adjacent environment that can be used for better operator guidance and feed-back during telemedicine applications and for superior overall clinical results by providing a common reference space for one or more medical instruments used during the clinical procedure and for data that is collected in time from one or more sensors. The virtual reality model may comprise multiple elements, among which are:

a contour 3-D model of the patient;
an interior 3-D model of the patient, that can be made of organ 3-D models, previously taken imaging data, current sensory data;
medical instruments and sensors, as they move in space and time;
data from sensors;
other elements that may guide the operator or may help the operator perform superior, reliable clinical procedure, such as virtual objects, rendered volumes, pointers, values, etc.
similar elements as in the previous points, but sent over a network from a remote user or computer system.

At the core of the embodiment is the use of a ranging camera and/or a passive camera, which is attached to either one of the medical instruments or sensors, or it is positioned to observe the environment comprising the patient, medical instruments, and potentially, the local clinician. This approach is exemplified by using an ultrasound imaging application.

FIGS. 10A-10B show examples of two ultrasound probe housings that comprises passive machine vision cameras and IMUs mechanically registered to the probe for probe tracking.

FIG. 10A shows an ultrasound probe housing assembly with a detachable camera housing shell. An ultrasound imaging probe housing shell 1001 is in contact with the investigated patient 1002 through the ultrasound probe head 1003 which comprises an ultrasound transducer. The ultrasound transducer can comprise a mechanically scanned transducer, a phased array of transducers, or a combination. Mechanically registered to the probe is a camera housing shell 1004 comprising a camera whose lenses 1005 are oriented in the general direction of the patient. In this embodiment, the communication with the ultrasound probe inside housing 1001 is done through a cable 1006, which can be an universal serial bus (USB) cable or other type of cable that goes to a read-out device. This read-out device can be a computing unit, such as a laptop, computer, tablet, or a smart phone, or a routing device when the housing 1001 of the probe comprises electronics able to create beam-forming signals to be sent to the transducers and to read-out and condition the signals received from the transducers. Otherwise, the read-out device will comprise beam forming and signal conditioning electronics, as well as a computing unit.

The data transport between the computing device and the camera can be done wirelessly or through a cable 1007, which can be an USB, FIREWIRE®, or other cable that ultimately sends the computer vision data to a computing unit that also receives data from the ultrasound probe.

An Inertial Measuring Unit (IMU) 1008 may be integrated into the probe housing shell 1001, into the camera housing shell 1004, or in any other way mechanically registered to the ultrasound probe. Here the IMU is shown inside the body of the ultrasound probe housing shell. The IMU could be used by itself, or in conjunction with the camera, or in conjunction with ultrasound speckle de-correlation analysis to determine the position and orientation of the ultrasound probe at each moment in time. For example, Kalman filters can be used to combine the positioning information form the computer vision subsystem and the IMU. Fiduciary elements can be placed on the patient or on stable objects adjacent to the patient to give a reference frame for the virtual reality model and to provide the proper scale for the whole environment when using the computer vision system for registering the ultrasound probe into the 3-D model. The fiduciary element can be made of a patterned layer made of various colors or shades, can comprise reflective objects, or active lighting elements, such as light emitting diodes (LEDs). Likewise, the fiduciary element can be rigid, flexible, or piece-wise rigid. Additionally, a miniature light projector, light source, LED or laser can be integrated into the system, such as into the body of the machine vision camera subsystem 104, to cast a light onto the field of view of the camera for better visualization.

In an alternative implementation, the fiduciary object may not be used, and in order to get calibration and scale information, the camera video stream is combined with the IMU data. In principle, it is possible to determine the position of the probe without the use of a fiduciary object, by analyzing the fixed visual features in the field-of-view. Examples of such features are room edges and corners, furniture, and lights. The computer vision algorithms can analyze the apparent position of these highlights to determine the position and orientation of the camera, and by simple transformations, of the probe.

FIG. 10B shows an embodiment of an ultrasound transducer with a machine vision and tracking subsystems integrated into the body of the housing for probe. The ultrasound imaging probe housing 1011 is in contact with the investigated patient 1012 through the ultrasound probe head. The body of the ultrasound transducer subsystem inside the ultrasound probe is represented schematically by dashed box 1013. The ultrasound transducer subsystem can comprise a mechanically scanned transducer, a phased array of transducers, or a combination of these.

Electronics for signal generation, signal conditioning, data processing and read-out may be placed inside the probe housing. A board 1014 accommodates all these electronics. This board can be connected to a cable 1015 that makes the connection to a computing unit or visualization device. Alternatively, the on-board electronics can communicate wirelessly with other computing and visualization units. An IMU is abstractly shown connected to the on board electronics 1014 as the dashed box 1016. A board 1017 accommodates the camera. This board can be electrically in contact with the board 1014. The body 1018 of the camera and lenses is within housing 1011. A visor 1019 on the ultrasound probe body allows light to penetrate into the lenses of the camera. Additionally, a button 1020 on the probe housing can be used for the user to interact with the functionalities of the system. For example, it can be used to start and stop the system, change acquisition modes, etc.

In another embodiment, ranging systems can be used to determine the contour of the patient and to track and spatially register the ultrasound probe in respect to the patient and other instruments.

FIGS. 11A-11C show examples of ultrasound imaging probes with tracking capability using ranging cameras mechanically registered to the ultrasound probe. In these embodiments, a ranging camera as described in FIG. 1 is used. The drawings of the figures show an ultrasound probe housing 1101 in contact with an investigated patient 1102.

FIG. 11A shows a lateral sectional view of the probe housing. FIG. 11B shows a front view of an embodiment with one ranging camera. FIG. 11C shows a front view of an embodiment with two cameras.

Unless specified, the following descriptions apply to all three figures. The ultrasound transducer subsystem 1103 is inside the body of the probe. The ultrasound transducer subsystem 1103 is connected to electronics comprising signal generation, signal conditioning, data processing and read-out components, also placed inside the probe housing shell. Dashed box 1104 is an abstract representation of such electronics. The data transfer between 1104 and a computing and visualization units can take place wirelessly or through a cable 1105.

The ranging camera is placed in camera housing shell 1106, which can be integrated into the ultrasound probe housing shell 1101, or can be mounted on it. In these embodiments, the housing shell comprising the ranging camera and tracking elements slides into a shoe 1107 on the ultrasound probe housing shell 1101 where it gets fixed with high mechanical registration. A board 1108 accommodates the ranging and tracking components. There are several components mounted on board 1108, including: a module that emits ranging signals 1109, a ranging sensor 1110, and an IMU 1111. A visor 1012 on the probe housing allows ranging signals (such as IR light) to penetrate into the lenses of the ranging camera 1110. A generic field of view for the ranging sensor is represented by the angle opening 1113.

The tracking subsystem board 1108 can be connected directly to read-out electronics or a computing unit through a cable 1114 or wirelessly. Alternatively, the board 1108 can be connected to the electronics inside the ultrasound probe housing shell 1101 through a connector assembly 1115. Whereas the cable 1116 makes the connection inside the tracking subsystem housing shell between the board 1108 and the connector 1115, the cable 1117 makes the connection inside the ultrasound probe housing shell 1101 between the connector 1115 and the board 1104 or between the connector 1115 and the read-out cable 1105, directly. The electrical connection inside the connection system 1115 can be made when the tracking subsystem housing shell 1106 is slid into the shoe 1107. Additionally, a button 1118 on the probe housing shell can be used for the user to interact with the functionalities of the system. For example, it can be used to start and stop the system, change acquisition modes, etc.

FIG. 11B shows a front view of the whole assembly showcasing a single ranging sensor. In a time of flight implementation, one or more light sources 1109 are part of the time of flight camera, whereas the light sensing component of the time of flight camera is behind the window 1112. When a structured light implementation is used, the level arm between the light source 1109 and the light sensor will be increased so that appropriate ranging performance is obtained for the range of distances of interest.

FIG. 11C shows a front view of the whole assembly showcasing two light sensors behind windows 1112 and 1119. In a time of flight ranging camera implementation, one or more light sources 1109 can be combined with two time of flight light sensors behind the windows 1112 and 1119. In a structured light ranging camera implementation, a structured light source 1109 can be combined with two light sensors behind the windows 1112 and 1119 on either side of the structured light source to create a stereoscopic structured light camera. This arrangement will insure overlap in the field of view of the structured light source with the field of view of at least one light sensor.

The ranging camera can use most preferably IR light, so that the light source 1109 is a IR light source, and light sensor is optimized to detect IR light. However, light or any color could be used. In a hybrid implementation that combines a ranging camera with a non-ranging camera, a ranging assembly can be made of one or more light sources 1109 and a ranging sensor behind window 1112, and the sensor behind window 1119 can be a non-ranging light sensor, such as a RGB (red green blue) or black-and-white (B/W) CMOS or CCD. In a pure machine vision camera implementation, a light source 1109 can be used mainly for scene illumination, with the sensors behind windows 1112 and 1119 forming a stereoscopic camera. In this case, stereoscopic machine vision algorithms can be used on the computing unit to analyze the data from the two sensors to create a dense, 3-D model of the contour of objects, and for spatial registration of the ultrasound probe in respect to the investigated patient.

The ranging and probe tracking embodiments, as exemplified in the figure can also be used in conjunction with other probes, such as gamma-probes for lymph node detection as described above and in FIG. 9.

FIG. 12 shows various ways in which an ultrasound probe with integrated tracking capabilities as exemplified above can be coupled to read-out, data processing and visualization units.

FIG. 12A shows a read-out which more closely integrates the streams from the tracking subsystem and ultrasound probe. The ultrasound probe assembly 1201 is shown with two cables, one 1202 primarily for ultrasound control and data read-out, and another one 1203 primarily for tracking subsystem control and data read-out. Two cables shown in the figure, but a single cable can also be used to carry all information. The two connections 1202 and 1203 connect to an electronics module 1204 comprising components for beam-forming, signal processing and data collection. Inside module 1204 data from the tracking subsystem and ultrasound probe can be time synchronized and associated with each other. The data connection 1206 transmits primarily tracking subsystem data between the data conditioning unit 1204 and the computing unit 1205. Likewise, data connection 1207 transmits primarily ultrasound probe scan data between the data conditioning unit 1204 and the computing unit 1205. Data connections 1206 and 1207 can use the same cable or connections, or separate connections. Units 1204 and 1205 can be physically separate, or integrated into a single device.

In some implementations, all or part of the electronics of 1204 can be integrated into the ultrasound probe housing. In that case, the connections 1202 and 1203 can link directly to the computing unit 1205. Examples of such a computing unit are: a computer, laptop, tablet, smart phone, or other custom processing unit. In some implementations, the computing unit itself can be integrated into the housing of the ultrasound probe assembly 1201.

Inside the computing unit 1205, algorithms and methods can be used to prepare ultrasound data for visualization, to register the ultrasound probe in respect to the patient by analyzing the probe tracking information, to build 3-D models of the patient, to allow users to control and manipulate ultrasound and tracking data, to store investigation data, to retrieve previously stored data, to provide connections with other computing units, internet or local network, servers, etc.

Figure 13:
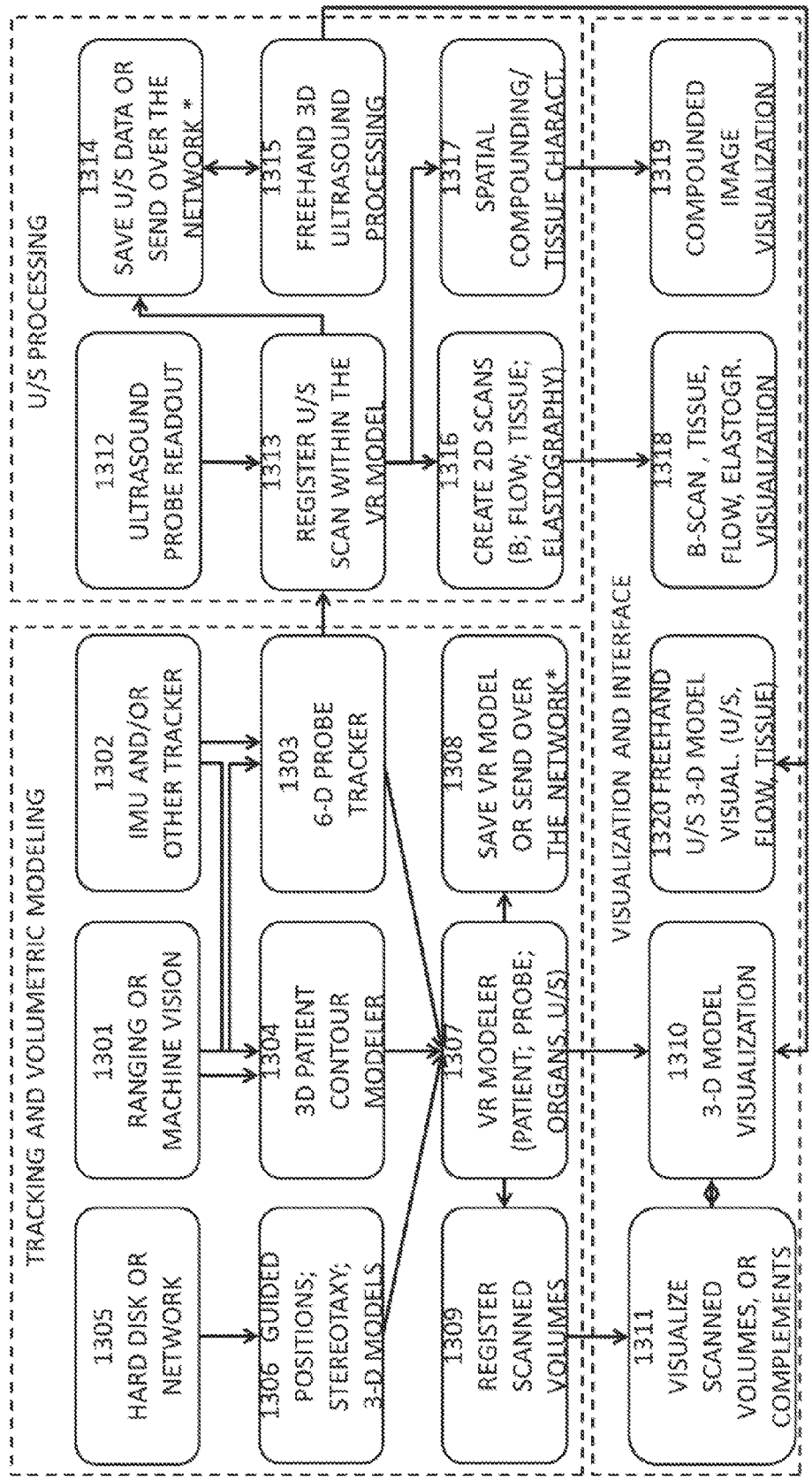
FIG. 13 is a diagram of ultrasound methods that use tracking and spatial registration capability in accordance with an embodiment.
Figure 14:
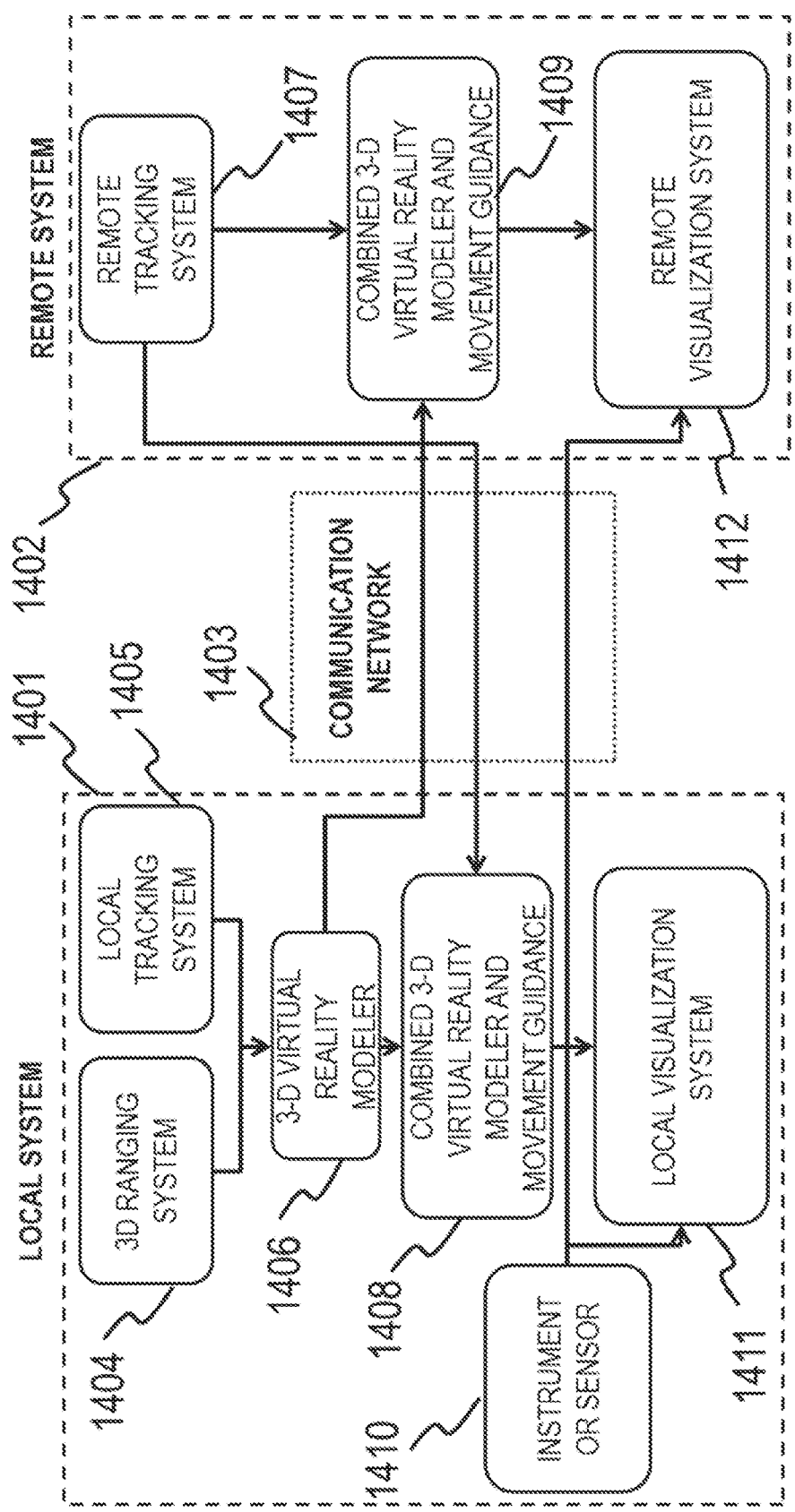
FIG. 14 is a system diagram of a data flow for a virtual reality based telemedicine and guidance system in accordance with an embodiment.

FIGS. 13 and 14 shows examples of such methods that can be implemented inside the computing unit.

A visualization device 1206 (see FIG. 12), such as a monitor, touch screen, projector, head mounted displays, goggles or augmented reality glasses can be used to visualize and interface with the data. The operator of the probe can interface with the system though a mouse/keyboard, touch screen, joystick of other non-contact devices, such as structured light or time of flight ranging systems that interpret the hand and finger movements of the operator.

FIG. 12B shows a read-out which does not closely integrate the streams from the tracking subsystem and ultrasound probe. This implementation is more suitable when the probe tracking capability and associated methods are implemented to existing ultrasound machines. Such implementation would allow existing ultrasound systems to be fitted with new ultrasound probes that have tracking capability.

The ultrasound probe assembly 1211 is shown with two cables, one 1212 primarily for ultrasound control and data read-out, and another one 1213 primarily for tracking subsystem control and data read-out. For existing ultrasound machines, there is normally limited capability to provide a connection for the tracking subsystem. Also, most commonly, the electronics module 1214 for beam-forming, signal processing and data collection and the computing unit 1215 for further processing and visualization are integrated into a common physical body.

Many commercial ultrasound machines provide an ultrasound scan output, such as a data or video output for the visualization of ultrasound scan and controls on external monitors. This output can be read-out by a second computing unit 1216 which also connects to the tracking subsystem through connection 1213. Methods for data synchronization, data processing, probe registration, 3-D model formation, data storage and retrieval, user interface, communication with other servers or computers, and connection to networks can be implemented inside unit 1216. Finally, a visualization device 1217, similar to 1206 can be used to visualize and interface with the data.

With the present invention, we also introduce new methods for ultrasound investigations, such as remote-guided ultrasound investigations, computer guided ultrasound investigations, ultrasound stereotaxy, freehand spatial compounding, tissue characterization, tissue elastometric property characterization, and enhanced freehand 3-D ultrasound. Many of these methods are made available by probe tracking techniques as introduced here, or other tracking techniques.

FIG. 13 shows an example of how such methods can be implemented in a computing device. The processes supporting the introduced methods can be separated in three main blocks: tracking and volumetric modeling, ultrasound processing, and visualization and interface. As exemplified in the figure, modules 1301 to 1309 are part of the tracking and volumetric modeling block, modules 1312 to 1317 are part of the ultrasound processing block, and 1310, 1311, 1318, 1319, 1320 are part of the visualization and interface block.

The data from the ranging system and/or machine vision system 1301 can be combined with the data from a tracker 1302, such as an IMU inside the 1303 processing module inside the computing unit, to create ultrasound probe tracking information. The combined data can also be used to build the 3-D outline of the patient inside module 1304. Other data stored on a local storage device or from the network 1305 can be loaded to support functionalities, such as expert guidance, remote guidance and ultrasound stereotaxy. This data is loaded into a gateway module 1306.

The probe tracking information from 1303, the patient contour information from 1304 and other stored information from 1306 can be merged to build a virtual reality (VR) model inside module 1307. This model can comprise the contour of the patient, models of the ultrasound probe in respect to the patient, 3-D or sectional organ models, current and previously stored ultrasound and other imaging models, other medical instruments, graphical user interface components, links to other data, and other linear, areal and volumetric components and measures. The VR model can be sent over the network, or locally saved in its whole or parts of it inside 1308 module. The data sent to module 1308 can be associated with other data, such as the ultrasound data of 1314. By keeping track of the volumetric elements scanned by the ultrasound system during an investigation, it is possible to build a 3-D model representing the volumes inside the patient that have been already investigated, and the volumes inside the patient that may require more investigation. This process is done inside module 1309. The VR model, or parts of it, can then be sent to a rendering and visualization module 1310. Likewise, the 3-D model representing investigated volumes or volumes that require more investigations is sent to a rendering and visualization module 1311. The two models can be co-registered and superposed inside a unified model.

Another analysis block in the figure includes ultrasound analysis processes. The ultrasound data stream coming from the ultrasound probe read-out 1312 is synchronized and associated with the probe tracking data stream so that the probe tracking information is appended to the ultrasound data bunches inside module 1313. The ensuing time- and position-registered ultrasound stream, which will be called a "spatially registered scan," can be sent over the network or saved locally on a storage device 1314. The VR model in its entirety or parts of it can be appended to the ultrasound data saved on the local storage device or sent over the network to another location. The ultrasound data can be analyzed to create 2-D scans, such as B-scans, elastography map, Doppler flow or other tissue characterization maps inside module 1316. The spatially registered ultrasound scans can be analyzed using spatial compounding methods to not only filter out ultrasound speckle and artifacts, but also to extract more accurate information about types of tissues inside module 1317. This can be done by analyzing multiple spatially registered scans that cover the same area from different ultrasound transducer positions and angles. In the present context, this spatial compounding analysis can be referred to as a limited scope 3-D freehand ultrasound.

The 2-D scans delivered by 1316 can then be visualized inside the visualization and interface module 1318. Likewise, the spatially compounded model or tissue type model delivered by 1317 can be visualized by module 1319. At each moment in time, the spatially compounded model to be visualized will be updated repeatedly to include the data from the latest spatially registered scans. For example, in one implementation, the user can observe on a visualization device the section of the compounded model or tissue type model that corresponds to the section being scanned at that moment by the ultrasound probe. In this way, the user can easily navigate the spatially compounded model or tissue type model by moving the ultrasound probe on the patient. Controls can be provided to the user to adjust visualization and processing settings for the tissue characterization maps.

The maps visualized by modules 1318 and 1319 can also be merged into a common visualization module.

By using most of the spatially registered ultrasound scans collected during an investigation, a full 3-D model can be created. This can be referred to as "freehand 3-D ultrasound imaging." This process is indicated in module 1315. The data can come from a local storage device, from the network, or directly from a memory. The process can take place off-line, but if computing resources are available, it can also take place in real-time. The output model can be saved on a local storage device, sent over the network, or sent to a visualization module 1320 optimized to visualize 3-D models, including tissue type, elastometric property, flow, or to the more generic VR visualization module 1310.

FIG. 14 gives an example of how some of the above methods can be integrated into a telemedicine and operator guidance system. The local system 1401 is the system setup at the place where the patient is treated or evaluated by the "local" clinician. The remote system 1402 is the system setup at the site of the "expert" remote clinician. The exchange of data is done through a communication network 1403. This can be, for example, an Internet network, a local computer network, or a wireless network. The Computer Vision System 1404 may provide 3-D models, such as patient 3-D contour, as well as probe tracking information.

The tracking information from 1404, if available, is combined with the tracking information delivered by the inertial measurement unit system 1405. A 3-D virtual modeler system 1406 merges the information from 1404 and 1405 into a combined 3-D model. This model is send over the communication network 1403 to the remote system 1402, where it is combined with tracking information provided by the remote tracking system 1407. The core purpose of the remote tracking system 1407 is to allow the remote clinician to communicate to the local clinician his or her choice in what regards the manipulation of a medical device, such as an ultrasound imaging probe. The data streamed out of 1407 will comprise the position and orientation of the probe, as elected by the remote clinician.

To create this stream of data, the remote user should have an intuitive way to do it. A machine vision system combined with an IMU tracking system similar to the setup at the "local" site will most probably be the most intuitive way. Using this implementation, the "remote" user will just have to move a mock-up medical instrument at the remote site in a similar fashion as the local clinician. For direct feed-back to the remote user, a combined 3-D virtual reality modeler and movement guidance system 1408 will include the position of the medical instrument proposed by the remote user into a common 3-D model. The position of the medical instrument proposed by the remote user delivered by 1407 will be sent over the network to the local system to be combined with the 3-D virtual model within the a combined 3-D virtual reality modeler and movement guidance system 1409, which is basically a mirror of the remote system 1408.

However, whereas the purpose of 1408 is to create feed-back to the remote user in what regards her/his proposed position of the medical instrument in respect to the 3-D model, the purpose of 1409 is to create information for the local operator she or he can use for guidance in how to manipulate the medical instrument. The stream of data coming from the medical instrument 1410 will be visualized locally by the local operator using a visualization system 1411. The combined 3-D model coming from 1409 will be visualized as well, preferably on the same device 1411. The remote user will monitor the visualization system 1412 to inspect the data taken by the medical instrument 1410, and to get feed-back on her or his manipulation of the probe mock-up that is part of the remote tracking system 1407. The visualization systems 1411 and 1412 can be screens, or augmented reality systems worn by operators or users.

The remote tracking system can utilize a similar tracking system as the local tracking system, or it can be implemented in several other ways. Examples are: a joystick, a computer mouse, a keyboard, a ranging device, or other human interfaces.

Figure 15:
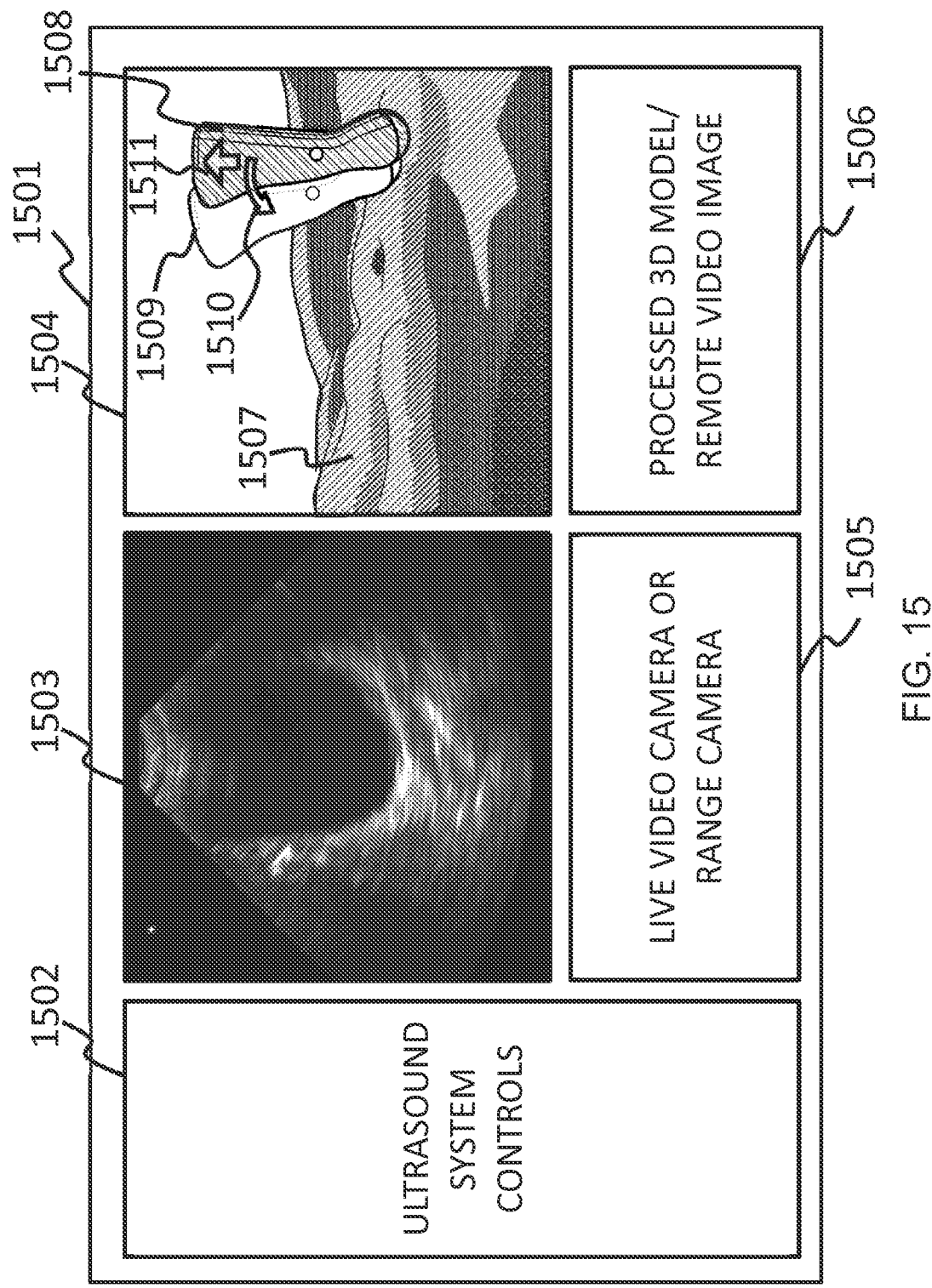
FIG. 15 illustrates a graphical user interface (GUI) for an ultrasound system with telemedicine, stereotactic and expert system guidance capabilities in accordance with an embodiment.

For the case when the medical instrument is an ultrasound scanner, an example of visualization and graphical user interface screen is shown in FIG. 15. The visualization area 1501 may comprise one or more windows and panels. In a more general implementation, the visualization area will comprise a panel 1502 containing buttons and links to settings and controls for the ultrasound system, computer vision system, IMU, visualization, data processing modules, etc. The ultrasound image 1503 may represent a regular B-scan, or a more advanced imaging output, such as a tissue type weighted image, fluid flow, tissue movement, tissue type, tissue elastometric properties, or a combination of any of these. The window 1504 shows a 3-D representation of the 3-D virtual model of the setup. Other windows can show footage of the computer vision or ranging camera in window 1505, and other data in window 1506, such as video image from the remote site, or processed ultrasound data, such as:

3-D or 2-D sections of a model of patient that can include models imported from other imaging modalities, such as computed tomography (CT), magnetic resonance imaging (MRI), positron emission tomography (PET), or single-photon emission computed tomography (SPECT);

3-D of 2-D tissue weighted images (tissue characterization and fluid flow);

representation of 3-D organ segmentation;

anomaly detection result;

volumetric rendering of volume that has been scanned;

volumetric rendering of volume that requires more scanning;

any section of any of these models of combination of them.

The window 1504 comprising the 3-D model of the patient can also comprise any of the elements described for window 1506, as well as 2-D ultrasound scans. The purpose of this window can be to guide the local clinician on the best position and orientation of the probe in respect the patient 1507. The best position and orientation of the probe is suggested either by the local analysis results, as indicated by a computer system, or as recommended by a remote user.

In window 1504, the 3-D model ultrasound probe 1508, is shown positioned in respect to the 3-D model of the patient 1507, as obtained by the tracking system. The recommended position of the probe is represented by the graphical guiding element 1509. The recommendation can be given by an automatic computer system, or by a remote user, as described in FIG. 3. To guide the local operator in how the probe 1508 must be moved, other visual and numeric elements can be shown, such as curved 1510 and directional arrows 1511, representing the rotation and translation the probe has to make to overlap the position of the virtual probe 1509. The geometrical appearance of these elements, such as the length and the width of the arrows 1510 and 1511, can give fast feed-back to the local operator on how large the movement of the probe must be until it overlaps the virtual probe 1509. Additionally, or alternatively, numerical values, such as amplitude of angles (in degrees) and measures of distances (in millimeters), each, in all three directions, can be overlapped to give the local operator information about movement of the probe must be until it overlaps the virtual probe 1509. A color code can be used to represent each of the three spatial directions for translations and each of the three angles for rotations, whether shown as numbers or geometric elements, such as the arrows 1510 and 1511.

Alternatively to using a monitor for visualization, an augmented reality system can be employed, so that the local operator can observe an overlay of relevant elements over a direct view of the clinical set-up. Examples of elements that can be overlaid are: models of medical instruments, such as the virtual probe 1509; numerical and graphical indicators, such as directional arrows 1510 and 1511; 3-D anatomical models; ultrasound images and models, and others.

One disadvantage of tele-guided ultrasound functionality is that a highly trained expert is still required to be available for the investigation. An alternative to that is to have a local computer guidance system that has preloaded procedures for a large array of clinical investigations. The patient contour as measured by the ranging or light sensing system can be matched to the outline of a generic human model. This will allow the computer guidance system to give precise instructions about the positioning and movement of the ultrasound probe in respect to the real patient model. Ultrasound anatomical landmarks observed in real-time can be matched in 3-D to landmarks in the 3-D models for a much more precise registration that will correct for organ movements and displacements due to variations in body habitus and position. An ultrasound image interpretation can be given by the local user, expert system, or later by a radiologist.

A "stereotactic ultrasound" instrument as described herein can allow the user to label features of interest in 3-D, and register them with respect to the patient model so that follow-up investigations can easily use those coordinates to re-evaluate medical conditions. The user can be given software tools to mark features in the 2-D ultrasound scan. Since the ultrasound probe position will be spatially registered to the 3-D model of the patient contour, the marked structure will be registered within the 3-D patient model. Moreover, the positioning of the ultrasound probe with respect to the body can be retained so that it can be reproduced by an operator at a later moment. Similarly to the computer guided ultrasound functionality explained above, ultrasound anatomical landmarks observed in real-time can be matched in 3-D to ultrasound landmarks previously stored during previous examinations, or to other 3-D models, for a much more precise registration that will correct for organ movements and displacements. Tools for volume segmentation and measurement can be used to quantitatively evaluate various conditions and to track changes in time.

An advantage of the ultrasound system, as exemplified above, is that it can be used very efficiently as a "freehand" 3-D ultrasound system. A "freehand ultrasound" uses a regular 2-D ultrasound probe as the operator moves it across the body of the patient. Combining successive 2-D ultrasound images, a 3-D model of the whole investigated volume is formed. Since a whole 3-D model will be created by keeping track of all 2-D scans, the final result of the investigation will be practically independent on the skill of the operator to take relevant ultrasound cross-sections, and to notice relevant features.

A tracking system, as described above, can make freehand 3-D imaging functionality possible in an inexpensive, operationally efficient way. Various 3-D ultrasound models, such a tissue type weighted image, fluid flow, tissue movement, tissue elastometry properties can be obtained by using the freehand ultrasound capability of the system. Moreover, a real-time 3-D modeling of the patient layout will help the freehand ultrasound imaging process by providing information about changes in the patient position and skin layout. These changes can occur, for example, because of forces applied on the patient skin, such as by the ultrasound probe, voluntary of involuntary changes in the patient position, and because of patient breathing. This capability will help prediction of organ movement, improving the quality of the 3-D ultrasound modeling.

Tracking methods and systems that use at least a camera or ranging device to track the relative position of instruments, sensor probes, objects or parts of a user in respect to each other, or in respect to the at least one camera or ranging device are proposed. The at least one camera or ranging device can be positioned in such a way as to observe the general area where instruments, sensor probes or objects of interest or being acted upon by the user are positioned. As such, the at least one camera or ranging device can be positioned on a mount or on an object adjacent to the general work area, or can be carried by a human or robotic user. Examples of the at least one camera or ranging devices are: visual color camera, visual B/W camera, IR camera, plenoptic camera, time-of-flight camera, stereoscopic camera, structured light camera, stereoscopic structured light camera, ultrasound trackers, or electromagnetic trackers, such as magnetic trackers or radio-frequency trackers.

A computing unit can be operatively coupled with a memory and the at least one camera or ranging device, the memory having instructions for execution by the at least one processor configured to determine a spatial position and orientation of the instruments, sensor probes, objects or parts of a user in respect to each other, or in respect to the camera. For better tracking capability, fiducial markers or objects can be mounted on instruments, sensor probes or objects of interest to better determine their position and orientation. Examples of fiducial markers are reflective objects, objects with distinct shapes, binary black and white or colored coded tags with distinct codes. To increase the effective field of view for the objects of interest, instruments or sensor probes, more than one fiducial element can be mounted or attached to each of these. For example, a cube like element can comprise tags on each of its surfaces, so that at least one tag can be seen from any angle by the at least one camera or ranging device.

In the case when the at least one camera or ranging device is an ultrasound tracker, ultrasound detectors mechanically registered to the objects, instruments or sensor probes will be used. In the case when the at least one camera or ranging device is an electromagnetic tracker, electromagnetic sensors mechanically registered to the objects, instruments or sensor probes will be used.

Tracking the location and orientation of instruments, sensor probes and investigated objects in respect to the at least one camera or ranging system is done using the methods described earlier in this invention. However, of relevance is mainly the relative location and orientation between instruments, sensor probes and investigated objects. This is achieved by transformations taking into account the position and orientation of each element in respect to the at least one camera or ranging system.

A computing unit can be operatively coupled with a memory and the at least one camera or ranging device, the memory having instructions for execution by the at least one processor configured to create a 3-D model of the setup, including a contour of the objects of interest, instruments, or sensor probes.

At least one processor can be operatively coupled with a memory and the at least one camera or ranging device, the memory having instructions for execution by the at least one processor configured to observe and analyze movements of interactivity elements, such as parts of user's body or other objects, interpreting those movements to activate a process inside the at least one processor. Examples of interactivity elements can be: fingers, arms, instruments, pens, sticks, styluses. In order for the user to properly interact with the computer by moving interactivity elements, a display operationally coupled to the at least one processor will show the position of these interactivity elements in respect to a graphical user interface element, virtually positioned in the same general space as the interactivity elements. The user will be given regular computer interactivity tools such as: click, scroll, navigate files, models or images, zoom-in, zoom-out, type, etc. The display can be a computer monitor, an augmented reality system, and a head-mounted display.

In one implementation, the at least one camera or ranging system can be part of a head-mounted tracking and visualization (HMTV) system. This HMTV system can comprise not only tracking and ranging components, but also a display that allows the user to see images of interest, VR models, graphical interfaces, an augmented reality model, or other elements of interest. In one implementation, the user can use objects, or parts of his or her body to interact with the computer by moving them in the field of view of the at least one camera or ranging system. For better tracking capability, and potentially for better interactivity with the computer, the HMTV can also comprise an IMU. For example, with the help of the IMU, or the head-mounted at least one camera or ranging device, or a combination of these, the user could employ head gestures to execute a process on the at least one processor.

Figure 16:
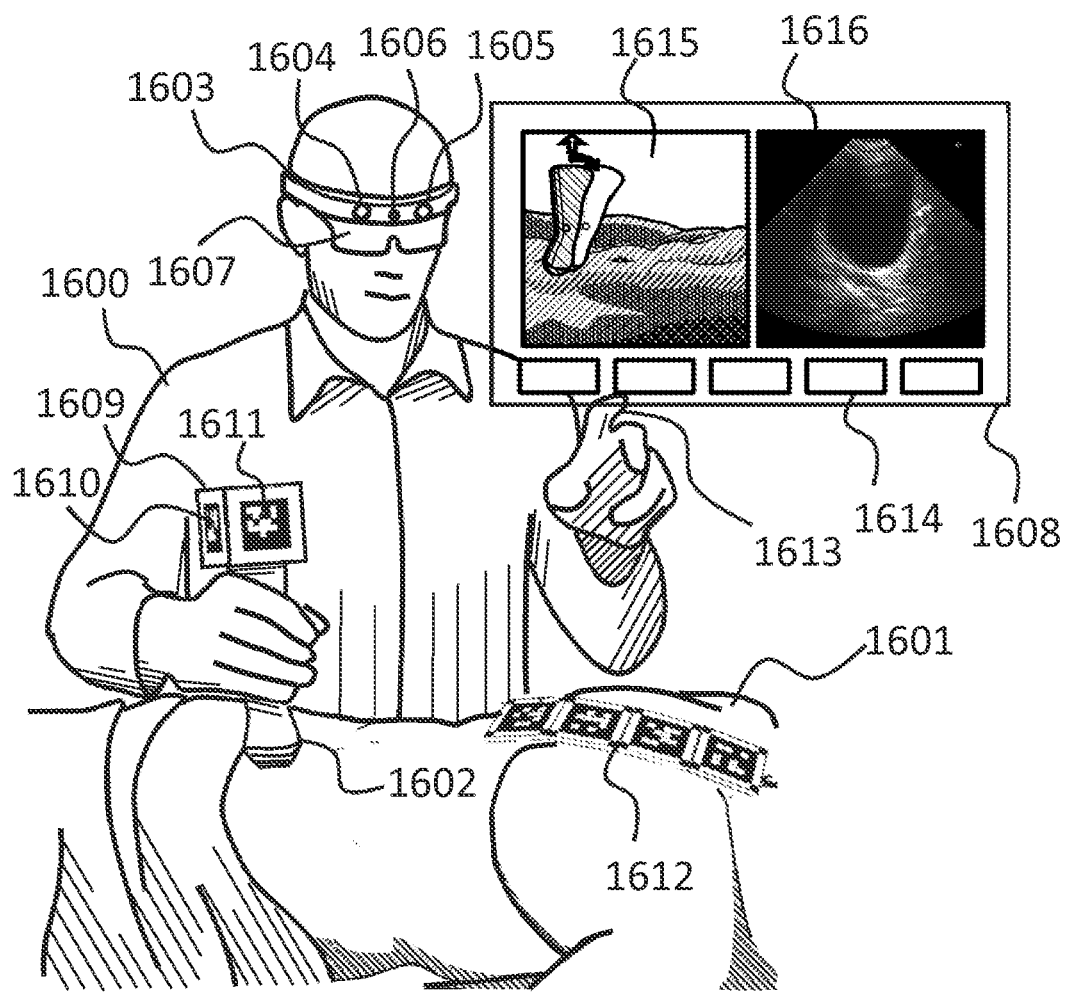
FIG. 16 illustrates a spatially registered medical investigation, where a camera or ranging system is supported by an operator's head-mounted tracking and visualization (HMTV) system in accordance with an embodiment.

FIG. 16 shows an example of an implementation where the at least one camera or ranging device is mounted on a HMTV system. For clarity, only one sensor probe is shown in this figure. A user 1600, such as a physician, investigates a object of interest 1601, such as a patient, using a sensor probe 1602, such as an ultrasound probe. The user wear a head mounted tracking and visualization system (HMTV) 1603, which comprises a camera system made out of two light sensing devices 1604 and 1605 and a light emitter 1606, which can be part of a structured light camera, a time of flight camera, a LIDAR sensing camera, or a flash LIDAR camera. More cameras could be used. This camera system can comprise a time of flight camera and a non-time-of-flight camera, a stereoscopic structured light system, a single camera structured light system and a visual camera, or any other combination. In this particular implementation the display 1607 is part of the HMTV system. Alternatively, or additionally, an external display can be used. The display 1607 can be a semitransparent display, can be an opaque display, or can be designed to only cover a part of the user's visual field of view. A representation of an image that could be shown by the display 1607 is shown inside the rectangle 1608.

The sensor probe 1602 carries a fiducial object 1609, mechanically registered to it, in the shape of a cube, on the surface of which distinct binary fiduciary tags are shown. In this figure, only two tags are visible: 1610 and 1611. This fiducial object can be part of the same housing shell as the sensor probe, can be part of a housing shell that mounts to the sensor probe housing shell in a similar fashion as camera housing shell 1004 or 1106, or can be mounted with a bracket on the sensor probe housing shell. In another implementation, both a fiducial object and a camera can be mechanically registered to the sensor probe or instrument. In another implementation, camera housing shells, such as 1004 or 1106) can be interchangeable with the fiducial object 1609. Another fiducial object 1612 in the form of a piece-wise rigid fiducial with distinct binary coding can be laid down or fixed to the investigated object 1601. The user 1600 can use his or her fingers 1613 as interactivity elements to interact with the computer (not shown). In one implementation, the computer could be carried by the user. In another implementation, the computer can be partially contained by the HMTV housing. In yet another implementation the computer can be placed inside the sensor probe housing 1602.

Buttons B1, B2, B3, B4, B5 showed by the display represent generic graphical user interface a user can virtually touch with interactivity elements 1613 to execute a process on the computer. For clarity, only button B4 is labeled by reference numeral 1614. The display 1607 also shows a 3-D virtual model 1615 or stereoscopic view of the setup, as it could be created by the camera system on the HMTV 1603, by itself, or in combination with other cameras or ranging systems mechanically registered to instruments or sensor probes, or mounted on other external objects. The purpose of this window can be also for computer and remote guidance as explained above. Window 1616 shows a scan delivered by the imaging sensor probe, in this case, this is an ultrasound scan.

Additionally, another tracking system, such as an IMU, can be mechanically registered to the HMTV or to the instrument and sensor probes for improved tracking performance, and for supplementary user interactivity with the computer.

When the sensor probe is an ultrasound transducer, many previous investigative modalities explained above can be used in this implementation. Correspondingly, this implementation can allow for remote and computer guidance, ultrasound stereotaxy, freehand spatial compounding, freehand tissue elastometry, freehand 3-D imaging, tissue characterization, as well as other applications, such as needle guidance using ultrasound, ultrasound assisted surgery, etc.

When the sensor is a gamma-ray probe, this implementation will allow the surgeon to visualize directly on the display the 3-D distribution of the radioactive tracer with respect to the body outline.

Stereotaxy, computer and remote guidance uses can also be found when the instrument or sensor probe is any of the following: hand-held imaging device, surgical instruments, laparoscopic instruments, etc.

Many other intraoperative uses of the presented methods and implementations can be found. These examples are non-limiting and show how the methods disclosed in this invention can be implemented in practice.

Alternative Modes

Another field where aspects of this invention can provide significant advantages is in environmental surveys. Spatial registration systems attached to surveying sensors can be used to automatically perform environmental surveys. The spatial registration system will conveniently provide the position and orientation of the system in relationship to the investigated objects or to the adjacent environmental objects, keeping an automatic log of the surveyed locations. This capability will also allow for an automatic mapping of the investigated features.

One particular example of an application that will benefit from such a capability is the measurement of the radioactive dose or radiation field inside structures. In such an application, among other sensors, any of the following sensors can be used: a radiation dosimeter, a spectroscopic detector, a radiation imaging system, a spectroscopic imaging system. Likewise, this capability can be used to map a chemical field using chemical or biological sensors.

Figure 17:
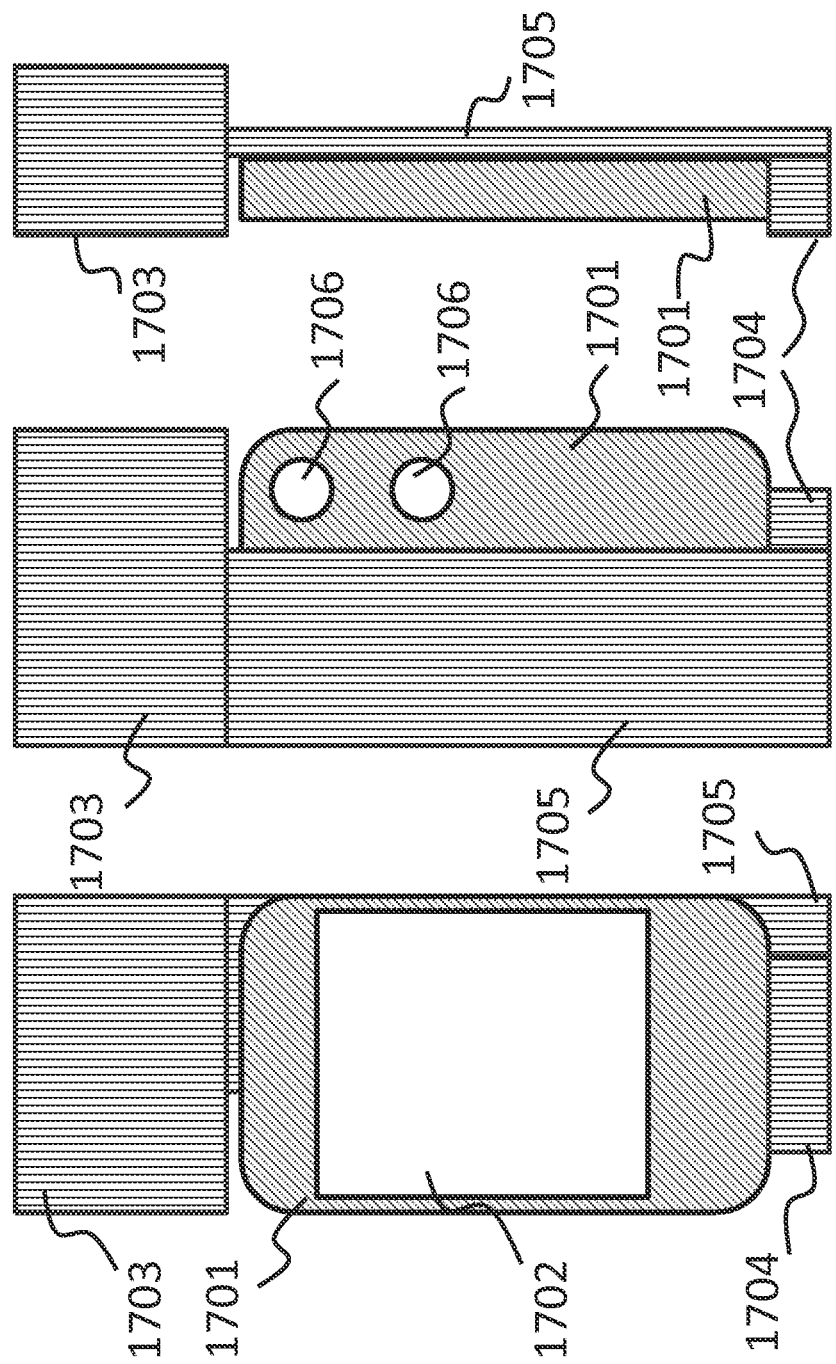
FIG. 17A illustrates a front view of a probe, such as a dosimeter, radiation detector or chemical sensor, attached to a smart phone in accordance with an embodiment.
FIG. 17B illustrates a rear view of the probe of FIG. 17A.
FIG. 17C illustrates a side view of the probe of FIG. 17A.

FIGS. 17A-17C illustrate a probe, such as a dosimeter, radiation detector or chemical sensor, attached to a smart phone in accordance with an embodiment. Here, a portable computer or a smart phone 1701 can be used for computer vision processing, for data visualization using its built-in screen 1702 and for video image capture using the built-in camera 1706. Where available, an extra built-in video camera 1707 can be used for stereoscopic implementations. A sensor probe 1703 is clipped on to the smart phone device 1701 with good mechanical registration through arm 1705 and connector body 1704.

Examples of probe sensors 1703 can be radiation detection devices, radiation dosimeters, radiation imagers, spectroscopic radiation imagers, chemical sensors, bio-chemical sensors, infra-red sensors, etc.

A software program on the smart phone or the equivalent portable computer can be used to acquire the data from the built-in video cameras and from the sensor probe. Furthermore, the program can contain the necessary computer vision algorithms to provide spatial registration and tracking of the sensors in respect to the investigated environment and objects. Having this, a field map of the investigated environment can be obtained. For example, if a radiation dosimeter is used as a sensor probe, a map of the radiation dose field is obtained. The map can be 1D, 2D or even 3D, as demanded by the application. Where the local processing power allows it, the processing can be done completely on board. Where local processing power is not sufficient to accommodate all software needs, raw or partially analyzed data can be sent wirelessly or through wires to another external processing unit.

Figure 18:
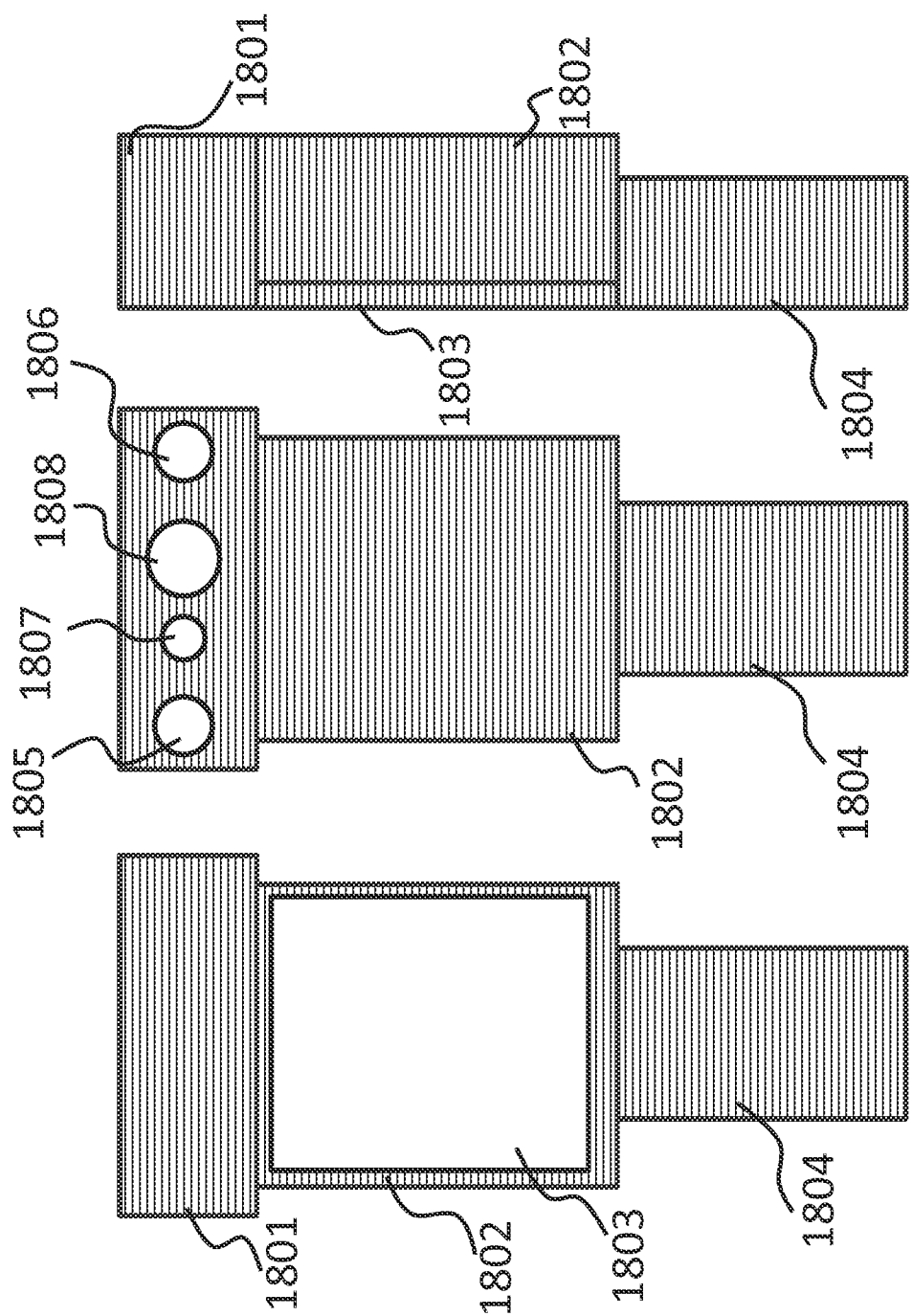
FIG. 18A illustrates a front view of a hand-held probe with an integrated spatial registration system in accordance with an embodiment.
FIG. 18B illustrates a rear view of the hand-held probe of FIG. 18A.
FIG. 18C illustrates a side view of the hand-held probe of FIG. 18A.

FIGS. 18A-18C show a hand-held probe with an integrated spatial registration system in accordance with an embodiment. Here, a dedicated hand-held device contains the spatial self-registration system body 1801, a body 1802 that comprises the sensor probe, data acquisition and processing unit (computer), and a handle 1804 that may comprise battery, voltage supply, or other sensors. A screen 1803 may be integrated for visualization and user interfacing. The spatial self-registration system may comprise one or more cameras 1805 and 1806, a laser beam source 1807, a sensor 1808 to detect reflected laser light. The laser beam assembly made of 1807 and 1808 can be used for laser ranging (lidar), for time of flight ranging, or for structured light ranging in order to obtain supplementary range information about the scene.

The data acquisition and analysis software can be implemented on board of the hand held device on the processing unit. Likewise, the algorithms for spatial self-registration can be implemented on board. Alternatively, the data can be sent wirelessly or through wires to other external processing units. As explained above, such system may also include an INU and a GPS sensor.

Figure 19:
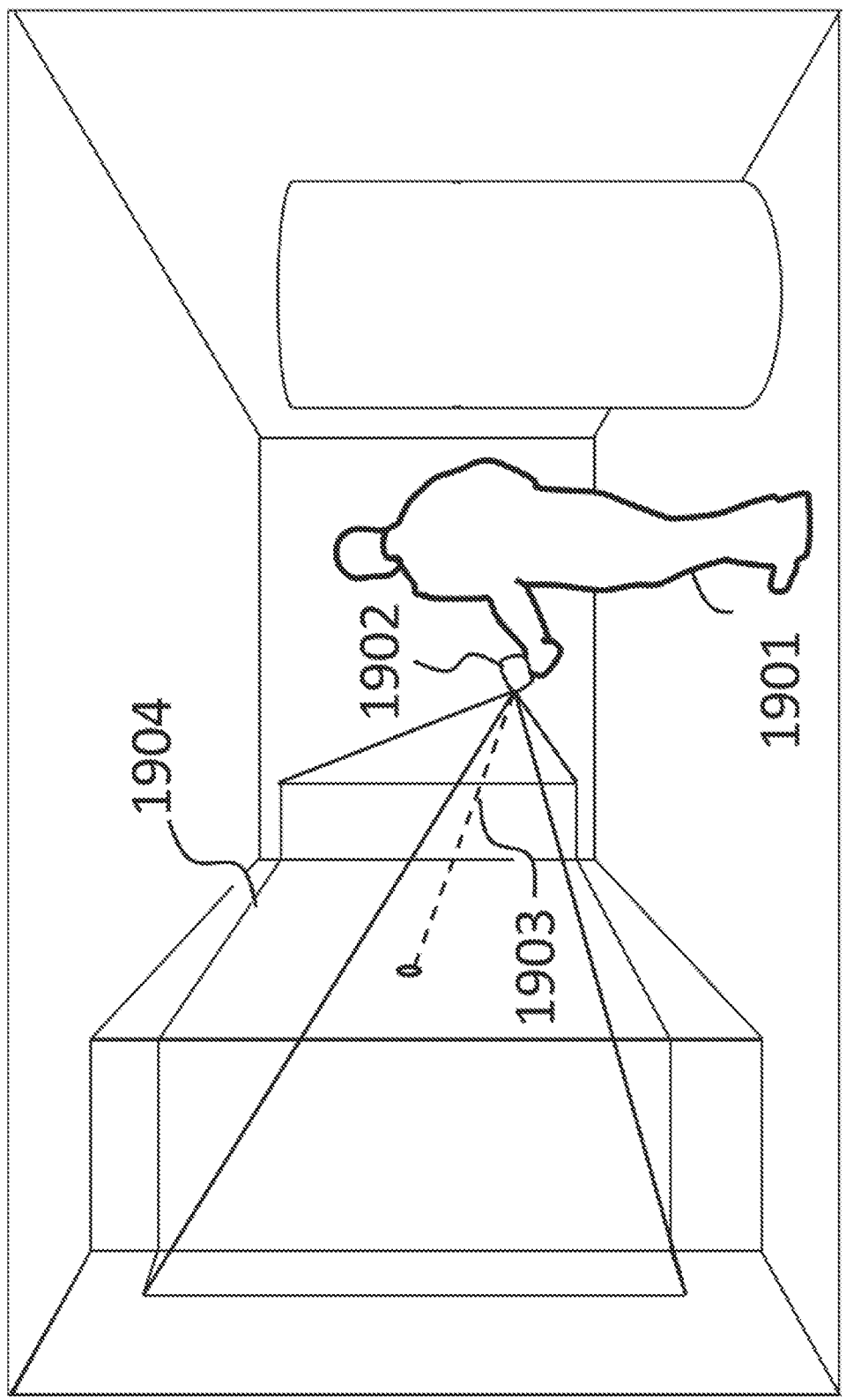
FIG. 19 illustrates use of a computer vision camera combined with a single beam lidar for hand-held probe spatial registration in accordance with an embodiment.

FIG. 19 illustrates a representation of the way the device shown in FIG. 7 can be used in practice. In a survey scenario, the user 1901 will hold the survey system 1902, such as a chemical sensor or a radiation dosimeter, that has self-registration capability (similarly to the device shown in FIG. 18) to scan the field but also to acquire information about the relative position of the sensor in the environment. The system 1902 may contain a lidar ranging system that points a laser beam 1903 to the adjacent objects. The video camera(s) integrated into the system 1902 may have a field of view represented by the lines 1904. A computer vision algorithm can be used to identify the laser spot in the visual picture allowing a match of the range information from the lidar with the features seen by the computer vision camera. This will allow absolute scaling of the 3D model delivered by the computer vision system.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A spatial registration apparatus, comprising:
a medical instrument or sensor probe;
a camera rigidly connected with the medical instrument or sensor probe;
a fiducial marker affixed to an object of interest, the object of interest being different from the medical instrument or sensor probe and different from the camera;
at least one first processor operatively coupled with a first memory, the first memory having first instructions for execution by the at least one first processor, wherein the first memory stores a relative location and orientation between the medical instrument or sensor probe and the rigidly connected camera, wherein the first instructions, when executed by the at least one first processor, cause the at least one first processor to determine a pose of the camera with respect to the fiducial marker using an image of the fiducial marker captured by the camera and then transform the pose, using the stored relative location and orientation between the medical instrument or sensor probe and the rigidly connected camera, to determine a first spatial position and orientation of the medical instrument or sensor probe with respect to the fiducial marker, the at least one first processor associating a first scan of the object of interest from the medical instrument or sensor probe with the first spatial position and orientation of the medical instrument or sensor probe to create a first spatially registered scan, the first scan being time synchronized with the first spatial position and orientation of the medical instrument or sensor probe;
a network; and
at least one second processor operatively coupled with a second memory, the second memory having second instructions for execution by the at least one second processor, the second instructions, when executed by the at least one second processor, cause the at least one second processor to derive visualization data from the first spatially registered scan from the medical instrument or sensor probe using the first spatial position and orientation of the medical instrument or sensor probe with respect to the fiducial marker, and display the visualization data, on a first display, to a first user.

2. The apparatus of claim 1, wherein the second instructions, when executed by the at least one second processor, cause the at least one second processor to produce a proposed spatial position and orientation of the medical instrument or sensor probe with respect to the fiducial marker.

3. The apparatus of claim 2, wherein the first instructions, when executed by the at least one first processor, cause the at least one first processor to display, on a second display, the visualization data and guidance elements indicating the proposed spatial position and orientation of the medical instrument or sensor probe with respect to the fiducial marker, to a second user.

4. The apparatus of claim 2, further comprising a mock-up instrument, a second camera rigidly connected with the mock-up instrument, and a second fiducial marker, wherein the second instructions, when executed by the at least one second processor, cause the at least one second processor to determine a second pose of the second camera with respect to the second fiducial marker using a second image of the second fiducial marker captured by the second camera and then transform the second pose, using a second relative location and orientation between the mock-up instrument and the second camera, the second relative location and orientation stored in the second memory, and wherein the production of the proposed spatial position and orientation by the at least one second processor is based on the second pose.

5. The apparatus of claim 2, further comprising an input device and a remote tracking system configured to track a position and orientation of the input device, wherein the production of the proposed spatial position and orientation by the at least one second processor is based on the tracked position and orientation of the input device, wherein the input device is one of a joystick, a mock-up instrument, and a computer mouse, and wherein the remote tracking system is one of a magnetic tracker, an electromagnetic tracker, an optical tracker, an inertial measurement unit, and a ranging camera.

6. The apparatus of claim 1, wherein the first instructions, when executed by the at least one first processor, cause the at least one first processor to render a three-dimensional model using the first spatially registered scan and a second spatially registered scan, the first spatially registered scan being from a first scanning plane of the medical instrument or sensor probe and the second spatially registered scan being from a second scanning plane of the medical instrument or sensor probe, the first scanning plane being different from the second scanning plane.

7. The apparatus of claim 6, wherein the first instructions, when executed by the at least one first processor, cause the at least one first processor to filter out a speckle or an artifact of the first spatially registered scan based on the second spatially registered scan.

8. The apparatus of claim 1, wherein a camera is configured to emit a signal and detect a reflection of the signal from the object of interest, and wherein the first instructions, when executed by the at least one first processor, cause the at least one first processor to determine a distance from the camera to at least three points on a surface of the object of interest based on the reflection of the signal.

9. The apparatus of claim 8, wherein the first instructions, when executed by the at least one first processor, cause the at least one first processor to determine a model of the surface of the object of interest based on the distance from the camera to the at least three points.

10. The apparatus of claim 8 wherein the first instructions, when executed by the at least one first processor, cause the at least one first processor to determine a second pose of the camera with respect to the object of interest based on the distance from the camera to the at least three points.

11. The apparatus of claim 1, wherein the second instructions, when executed by the at least one second processor, cause the at least one second processor to receive, via the network, the first spatially registered scan.

12. A spatial registration method, comprising:
storing, in a first memory, a relative location and orientation between a medical instrument or sensor probe and a camera rigidly connected with the medical instrument or sensor probe;
determining, by at least one first processor, a pose of the camera with respect to a fiducial marker using an image of the fiducial marker captured by the camera, the fiducial marker being affixed to an object of interest, the object of interest being different from the medical instrument or sensor probe and different from the camera;
transforming, by at least one first processor, the pose, using the stored relative location and orientation between the medical instrument or sensor probe and the rigidly connected camera, to determine a first spatial position and orientation of the medical instrument or sensor probe with respect to the fiducial marker;
associating, by at least one first processor, a first scan from the medical instrument or sensor probe with the first spatial position and orientation of the medical instrument or sensor probe to create a first spatially registered scan, the first scan being time synchronized with the first spatial position and orientation of the medical instrument or sensor probe;
deriving, by at least one second processor, visualization data from the first spatially registered scan from the medical instrument or sensor probe using the determined current spatial position and orientation of the medical instrument or sensor probe with respect to the fiducial marker; and
displaying the visualization data, on a first display, to a first user.

13. The method of claim 12, further comprising producing, by the at least one second processor, a proposed spatial position and orientation of the medical instrument or sensor probe with respect to the fiducial marker.

14. The method of claim 13, further comprising displaying, on a second display, the visualization data and guidance elements indicating the proposed spatial position and orientation of the medical instrument or sensor probe with respect to the fiducial marker, to a second user.

15. The method of claim 13, further comprising:
determining, by the at least one second processor, a second pose of a second camera with respect to a second fiducial marker using a second image of the second fiducial marker captured by the second camera, the second camera being rigidly connected with a mock-up instrument; and
transforming, by the at least one second processor, the second pose, using a second relative location and orientation between the mock-up instrument and the second camera, wherein the producing of the proposed spatial position and orientation by the at least one second processor is based on the second pose.

16. The method of claim 13, further comprising tracking, by a remote tracking system, a position and orientation of an input device, wherein the producing of the proposed spatial position and orientation by the at least one second processor is based on the tracked position and orientation of the input device, wherein the input device is one of a joystick, a mock-up instrument, and a computer mouse, and wherein the remote tracking system is one of a magnetic tracker, an electromagnetic tracker, an optical tracker, an inertial measurement unit, and a ranging camera.

17. The method of claim 12, further comprising rendering, by the at least one first processor, a three-dimensional model using the first spatially registered scan and a second spatially registered scan, the first spatially registered scan being from a first scanning plane of the medical instrument or sensor probe and the second spatially registered scan being from a second scanning plane of the medical instrument or sensor probe, the first scanning plane being different from the second scanning plane.

18. The method of claim 17, further comprising filtering, by the at least one first processor, out a speckle or an artifact of the first spatially registered scan based on the second spatially registered scan.

19. The method of claim 12, further comprising:
emitting, by the camera, a signal;
detecting, by the camera, a reflection of the signal from the object of interest; and
determining, by the at least one first processor, a distance from the camera to at least three points on a surface of the object of interest based on the reflection of the signal.

20. The method of claim 19, further comprising determining, by the at least one first processor, a model of the surface of the object of interest based on the distance from the camera to the at least three points.

21. The method of claim 19, further comprising determining, by the at least one first processor, a second pose of the camera with respect to the object of interest based on the distance from the camera to the at least three points.

22. The method of claim 12, further comprising receiving by the at least one second processor, via a network, the associated first spatially registered scan.

23. A hand-held spatial registration apparatus, comprising:
a fiducial marker affixed to an object of interest;
a medical instrument or sensor probe that is different from the object of interest;
a camera connected with the medical instrument or sensor probe and configured to capture images of the fiducial marker indicating distances between the camera and the fiducial marker;
a memory storing instructions and a relative location and orientation between the medical instrument or sensor probe and the rigidly connected camera; and
a processor operatively coupled with the memory and configured to execute the instructions to:
determine a first pose of the camera with respect to the fiducial marker based on a first image of the fiducial marker captured by the camera,
transform the first pose, using the stored relative location and orientation between the medical instrument or sensor probe and the rigidly connected camera, to determine a first spatial position and orientation of the medical instrument or sensor probe with respect to the fiducial marker,
generate a first spatially registered scan by associating a first scan from the medical instrument or sensor probe with the first pose,
determine a second pose of the camera with respect to the fiducial marker based on the second image of the fiducial marker captured by the camera,
transform the second pose, using the stored relative location and orientation between the medical instrument or sensor probe and the rigidly connected camera, to determine a second spatial position and orientation of the medical instrument or sensor probe with respect to the fiducial marker, the second spatial position and orientation being different from the first spatial position and orientation,
generate a second spatially registered scan by associating a second scan from the medical instrument or sensor probe with the second pose, and
render a three-dimensional model using the first spatially registered scan and the second spatially registered scan, the first spatially registered scan being from a first scanning plane of the medical instrument or sensor probe, the second spatially registered scan being from a second scanning plane of the medical instrument or sensor probe, the first scanning plane being different from the second scanning plane.

24. The apparatus of claim 23, wherein the processor is further configured to execute the instructions to display, on a display, the three-dimensional model and guidance elements indicating a third spatial position and orientation of the medical instrument or sensor probe with respect to the fiducial marker, the third spatial position and orientation being different from the first spatial position and orientation and the second spatial position and orientation.

* * * * *